United States Patent
Park et al.

(10) Patent No.: US 11,655,478 B2
(45) Date of Patent: *May 23, 2023

(54) PROMOTER DERIVED FROM ORGANIC ACID-RESISTANT YEAST AND METHOD FOR EXPRESSION OF TARGET GENE BY USING SAME

(71) Applicant: SK INNOVATION CO., LTD., Seoul (KR)

(72) Inventors: Jae Yeon Park, Daejeon (KR); Tae Young Lee, Daejeon (KR); Ki Sung Lee, Daejeon (KR); Outi Koivistoinen, Espoo (FI); Kari Koivuranta, Espoo (FI)

(73) Assignee: SK Innovation Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/047,805

(22) PCT Filed: Feb. 28, 2019

(86) PCT No.: PCT/KR2019/002432
§ 371 (c)(1),
(2) Date: Oct. 15, 2020

(87) PCT Pub. No.: WO2019/203435
PCT Pub. Date: Oct. 24, 2019

(65) Prior Publication Data
US 2021/0108216 A1    Apr. 15, 2021

(30) Foreign Application Priority Data
Apr. 17, 2018    (KR) .................. 10-2018-0044508

(51) Int. Cl.
*C12N 1/20* (2006.01)
*C12N 15/81* (2006.01)
*C12N 9/04* (2006.01)
*C12N 9/02* (2006.01)
*C12P 7/42* (2006.01)

(52) U.S. Cl.
CPC ......... *C12N 15/815* (2013.01); *C12N 9/0006* (2013.01); *C12N 9/0008* (2013.01); *C12N 15/81* (2013.01); *C12P 7/42* (2013.01); *C12Y 101/01001* (2013.01); *C12Y 101/01027* (2013.01); *C12Y 102/01075* (2013.01)

(58) Field of Classification Search
CPC ......... C12N 15/75; C12N 15/62; C12N 15/81
See application file for complete search history.

(56) References Cited

U.S. PATENT DOCUMENTS

| | | | |
|---|---|---|---|
| 7,049,108 B2 | 5/2006 | Porro et al. | |
| 7,141,410 B2 | 11/2006 | Rajgarhia et al. | |
| 7,232,664 B2 | 6/2007 | Van Hoek et al. | |
| 7,534,597 B2 | 5/2009 | Hause et al. | |
| 8,137,953 B2 | 3/2012 | Miller et al. | |
| 9,353,388 B2 | 5/2016 | Kim et al. | |
| 9,617,570 B2 | 4/2017 | Lim et al. | |
| 9,758,770 B2 | 9/2017 | Lim et al. | |
| 2003/0032152 A1 | 2/2003 | Porro et al. | |
| 2003/0190630 A1 | 10/2003 | Rajgarhia et al. | |
| 2009/0053782 A1 | 2/2009 | Dundon et al. | |
| 2012/0058529 A1 | 3/2012 | Ikushima et al. | |
| 2012/0214214 A1 | 8/2012 | Hara et al. | |
| 2012/0295319 A1 | 11/2012 | Nevoigt et al. | |
| 2013/0071893 A1 | 3/2013 | Lynch et al. | |
| 2015/0064752 A1 | 3/2015 | Lee et al. | |
| 2015/0152447 A1 | 6/2015 | Kim et al. | |
| 2016/0024484 A1 | 1/2016 | Lim et al. | |
| 2016/0333380 A1 | 11/2016 | Chung et al. | |
| 2021/0155945 A1* | 5/2021 | Park .................. | C12N 15/81 |
| 2021/0324346 A1 | 10/2021 | Park et al. | |
| 2021/0403882 A1 | 12/2021 | Park et al. | |
| 2022/0049262 A1 | 2/2022 | Park et al. | |
| 2022/0056459 A1 | 2/2022 | Park et al. | |

FOREIGN PATENT DOCUMENTS

| | | | |
|---|---|---|---|
| EP | 2873725 A1 | 5/2015 | |
| EP | 3795689 A1 | 3/2021 | |
| EP | 3808852 A1 | 4/2021 | |
| EP | 3865577 A2 | 8/2021 | |
| EP | 3896166 A1 | 10/2021 | |
| JP | 2001204464 A | 7/2001 | |

(Continued)

OTHER PUBLICATIONS

Jiang, Min et al. "Progress of succinic acid production from renewable resources: metabolic and fermentative strategies." Bioresource Technology 245 (2017): 1710-1717.
Zhang, Kechung et al. "A synthetic metabolic pathway for production of the platform chemical isobutyric acid." ChemSusChem 4.8 (2011): 1068-1070.
Zelle RM., et al. "Malic acid production by *Saccharomyces cerevisiae*: engineering of pyruvate carboxylation, oxaloacetate reduction, and malate export." Applied and Environmental Microbiology 74.9 (2008): 2766-2777.
Steiger M. G., et al. (2013). Biochemistry of microbial itaconic acid production. Frontiers in microbiology, 4, 23.
Nishant K. T., et al. (2010). The baker's yeast diploid genome is remarkably stable in vegetative growth and meiosis. PLoS Genet, 6(9), e1001109.

(Continued)

*Primary Examiner* — Tekchand Saidha
(74) *Attorney, Agent, or Firm* — The Webb Law Firm

(57) ABSTRACT

The present invention relates to a novel promoter for regulating ADH gene expression in an organic acid-resistant yeast, and a method of producing an organic acid by expressing an organic acid production-related gene using the same. When an organic acid production-related target gene is expressed in the organic acid-resistant yeast using the novel promoter according to the present invention, there is an advantage in that the yeast can produce the organic acid with high efficiency while having resistance to the organic acid without inhibiting the growth ability of the yeast.

9 Claims, 9 Drawing Sheets

Specification includes a Sequence Listing.

(56) References Cited

FOREIGN PATENT DOCUMENTS

| | | | |
|---|---|---|---|
| JP | 2005-137306 A | 6/2005 |
| JP | 4700395 B2 | 10/2006 |
| JP | 4095889 B2 | 6/2008 |
| JP | 4692173 B2 | 6/2011 |
| KR | 101576186 B1 | 12/2015 |
| KR | 10-2016-0012561 A | 2/2016 |
| KR | 10-2016-0133308 A | 11/2016 |
| KR | 101686900 B1 | 12/2016 |
| KR | 10-2016-0075640 A | 1/2017 |
| KR | 10-2017-0025315 A | 3/2017 |
| KR | 1020170077599 A | 7/2017 |
| KR | 10-2018-0015591 A | 2/2018 |
| KR | 1020190121031 A | 10/2019 |
| KR | 102140596 B1 | 8/2020 |
| KR | 1020210041903 A | 4/2021 |
| KR | 1020210128742 A | 10/2021 |
| WO | 9914335 A1 | 3/1999 |
| WO | 2005052174 A3 | 6/2005 |
| WO | 2007117282 A2 | 10/2007 |
| WO | 2019203436 A1 | 10/2019 |
| WO | 2020075986 A2 | 4/2020 |

OTHER PUBLICATIONS

Storchova Z "Ploidy changes and genome stability in yeast." Yeast 31.11 (2014): 421-430.
Abbott, D.A., et al., Metabolic engineering of Saccaromyces cerevisiae for producti nof cabbxylic acids: current status and challenges. FEMS Yeast Research 2009, vol. 9, pp. 1123-1136.
Samuel et al. "Applications and statistics for multiple high-scoring segments in molecular sequences." Proceedings at the National Academy of Sciences 90.12 (1993): 5873-5877.
Hyland P, Development of a Platform Strain for Production of Adipic Acid Yields Insights into the Localized Redox Metabolism of S. cerevisiae. Diss., University of Toronto (2013).
International Search Report dated May 30, 2019 for corresponding PCT patent application No. PCT/KR2019/002432.
Expanded European Search Report dated Jan. 5, 2022 in corresponding EP application No. 19 787 990.1.
Devos et al. "Practical Limits of Function Prediction" Proteins: Structure, Function and Genetics, 2000, vol. 41: 98-107.
Feldman-Salit et al. "Regulation of the activity of lactate dehydrogenases from four lactic acid bacteria" Journal of Biological Chemistry 288.29 (2013): 21295-21306.
Garvie, E. I. "Bacterial lactate dehydrogenases", Microbiological Reviews 44.1 (1980):106-139.
Ishida et al. "Efficient production of L-lactic acid by metabolically engineered Saccharomyces cerevisiae with a genome-integrated L-lactate dehydrogenase gene" Applied and Environmental Microbiology 71.4 (2005): 1964-1970.
Kisselev, L. "Polypeptide Release Factors in Prokaryotes and Eukaryotes: Same Function, Different Structure" Structure, 2002, vol. 10: 8-9.
Sauer et al. "16 years research on lactic acid production with yeast—ready for the market?" Biotechnology and Genetic Engineering Reviews 27.1 (2010): 229-256.
Savijoki et al. "Molecular genetic characterization of the L-lactate dehydrogenase gene (IdhL) of Lactobacillus heveticus and biochemical characterization of the enzyme" Applied and Environmental Microbiology 63.7 (1997): 2850-2856.
Skory, C. D. "Lactic acid production by Saccharomyces cerevisiae expressing a Rhizopus oryzae lactate dehydrogenase gene" Journal of Industrial Microbiology and Biotechnology 30.1 (2003): 22-27.
Skory et al. "Inhibition of Rhizopus lactate dehydrogenase by fructose 1,6-bisphosphate" Enzyme and Microbial Technology 44 (2009): 242-247.
Tokuhiro et al. "Double mutation of the PDC1 and ADH1 genes improves lactate production in the yeast Saccharomyces cerevisiae expressing the bovine lactate dehydrogenase gene" Applied Microbiology and Biotechnology 82.5 (2009): 883-890.
Whisstock et al. "Prediction of protein function from protein sequence and structure" Quarterly Reviews of Biophysics, 2003, vol. 36 (3): 307-340.
Witkowski et al. "Conversion of a Beta-Ketoacyl Synthase to a Malonyl Decarboxylase by Replacement of the Active-Site Cysteine with Glutamine" Biochemistry, 1999, 38: 11643-11650.
Zhang et al. "Adaptive mutations in sugar metabolism restore growth on glucose in a pyruvate decarboxylase negative yeast strain" Microbial Cell Factories 14.1 (2015): article 116, 11 pages.
Albertyn et al., "GPD1, which encodes glycerol-3-phosphate dehydrogenase, is essential for growth under osmotic stress in Saccharomyces cerevisiae, and its expression is regulated by the high osmolarity glycerol response pathway". Molecular and cellular biology, 1994, pp. 4135-4144.
Baek et al., "Metabolic engineering and adaptive evolution for efficient production of D-lactic acid in Saccharomyces cerevisiae". Applied Microbiology and Biotechnology, 2016, pp. 2737-2748, vol. 100.
Costenoble et al., "Microaerobic glycerol formation in Saccharomyces cerevisiae", Yeast, 2000, pp. 1483-1495, vol. 16.
Dexter et al., "Robust network structure of the Sln1-Ypd1-Ssk1 three-component phospho-relay prevents unintended activation of the HOG MAPK pathway in Saccharomyces cerevisiae", BMC Systems Biology, 2015, pp. 1-15, vol. 9, No. 17.
Guiard, B., "Structure, expression and regulation of a nuclear gene encoding a mitochondrial protein: the yeast L(+) lactate cytochrome c oxidoreductase (cytochrome b2)," Embo J., 1985, pp. 3265-3272, vol. 12.
Halestrap, A.P., The monocarboxylate transporter family—Structure and Functional Characterization, IUBMB Life, 2012, pp. 1-9, vol. 64, No. 1.
Hoppner et al., "Purification and kinetic characteristics of pyruvate decarboxylase and ethanol dehydrogenase from Zymomonas mobilis in relation to ethanol production", European Journal of Applied Microbiology and Biotechnology, 1983, pp. 152-157, vol. 17.
Hubmann et al., "Identification of multiple interacting alleles conferring low glycerol and high ethanol yield in Saccharomyces cerevisiae ethanolic fermentation", Biotechnology for Biofuels, 2013, pp. 1-17, vol. 6, No. 87.
Hubmann et al., "Quantitative trait analysis of yeast biodeversity yields novel gene tools for metabolic engineering," Metabolic Engineering, 2013, pp. 68-81, vol. 17.
Lodi et al., "Isolation of the DLD gene of Saccharomyces cerevisiae encoding the mitochondrial enzyme D-lactate ferricytochrome c oxidoreductase", Mol. Gen. Genet., 1993, pp. 315-324, vol. 238.
NCBI, GenBank Accession No. SMN19920.1, similar to Saccharomyces cerevisiae YLR044C PDC1 Major of three pyruvate decarboxylase isozymes, key enzyme in alcoholic fermentation, decarboxylates pyruvate to acetaldehyde [Kazachstania saulgeensis], 2017.
Ookubo et al., "Improvement of L-lactate production by CYB2 gene disruption in a Recombinant Saccharomyces cerevisiae Strain under low pH condition", Biosci. Biotechnol. Biochem., 2008, pp. 3063-3066, vol. 72, No. 11.
Pacheco et al., Lactic Acid production in Saccharomyces cerevisiae is modulated by expression of the monocarxboxylate transporter Jeni and Ady2, FEMS Yeast Res, 2012, pp. 375-381, vol. 12.
Park et al., "Low-pH production of D-lactic acid using newly isolated acid tolerant yeast Pichia kudriavzevii NG7", Biotechnology and Bioengineering, 2018, pp. 2232-2242, vol. 115.
Shen et al., "Effect on electrospun fibres by synthesis of high branching polylactic acid," R. Soc. Open Sci, 2018, pp. 1-13, vol. 5.
Valli et al., "Improvement of Lactic acid production in Saccharomyces cerevisiae by cell sorting for high intracellular pH", Appl Environ Microbiol, 2006, pp. 5492-5499, vol. 72, No. 8.
Van Maris et al., "Mini-review Microbial export of lactic and 3-hydroxypropanoic acid: implication for industrial fermentation processes", Metabolic Engineering, 2004, pp. 245-255, vol. 6.

(56) References Cited

OTHER PUBLICATIONS

Abbott et al., "Catalase Overexpression Reduces Lactic Acid-Induced Oxidative Stress in *Saccharomyces cerevisiae*". Applied and Environmental Microbiology, 2009, pp. 2320-2325, vol. 75, No. 8.

Fletcher et al., "Evolutionary engineering reveals divergent paths when yeast is adapted to different acidic environments", Metabolic Engineering, 2017, pp. 1-37.

Gao et al., "Zinc finger protein 637 protects cells against oxidative stress-induced premature senescence by mTERT-mediated telomerase activity and telomere maintenance", Cell Death and Disease, 2014, pp. 1-13, vol. 5, No. e1334.

Uniprot, Accession No. A0A1X7R452,2019, www.uniprot.org.

Lee et al.,"Co-expression of two heterologous lactate dehydrogenases genes in Kluyveromyces marxianus for L-lactic acid production", J. Biotechnology, 2017, pp. 81-86, vol. 241.

Long et al., "How adaptive evolution reshapes metabolism to improve fitness: recent advances and future outlook" Current Opinion in Chemical Engineering, 2018, pp. 209-215, vol. 22.

Prasad et al., "Molecular Mechanisms of Zinc as a Pro-Antioxidant Mediator: Clinical Therapeutic Implications", Antioxidants, 2019, pp. 1-22, vol. 8, No. 164.

Van Maris et al., "Homofermentative Lactate Production Cannot Sustain Anaerobic Growth of Engineered *Saccharomyces cerevisiae*: Possible Consequence of Energy-Dependent Lactate Export", Appl. Environ. Microbiol., 2004, pp. 2898-2905, vol. 70, No. 5.

Zhu et al., "Evolutionary engineering of industrial microorganism-strategies and applications", Applied Microbiology and Biotechnology, 2018, pp. 4615-4627.

Zhou et al., "Selective Sensitization of Zinc Finger Protein Oxidation by ROS Through Arsenic Binding", The Journal of Biological Chemistry, 2015, pp. 18361-18369, vol. 290.

Nevoigt et al., "Osmoregulation and glycerol metabolism in the yeast *Saccharomyces cerevisiae*", FEMS Microbiology Reviews, 1997, pp. 231-241, vol. 21.

Pearson, "Effective protein sequence comparison", Methods Enzymology, 1996, pp. 227-258, vol. 266.

GenEmbl Accession No. CP024408,2017.

\* cited by examiner

[Fig. 1]
(a)
(b)
(c)
(d)
(e)
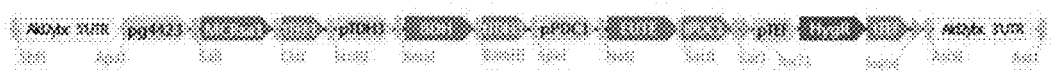

[Fig. 2]
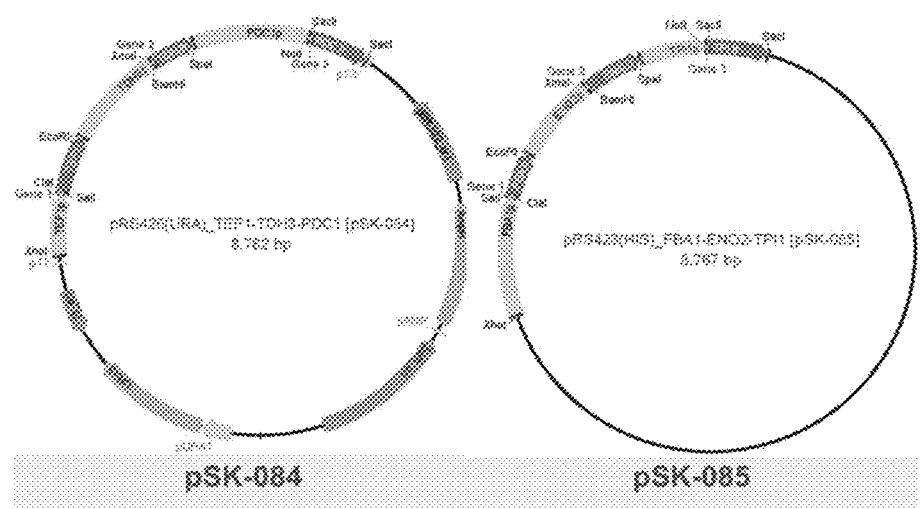

[Fig. 3]
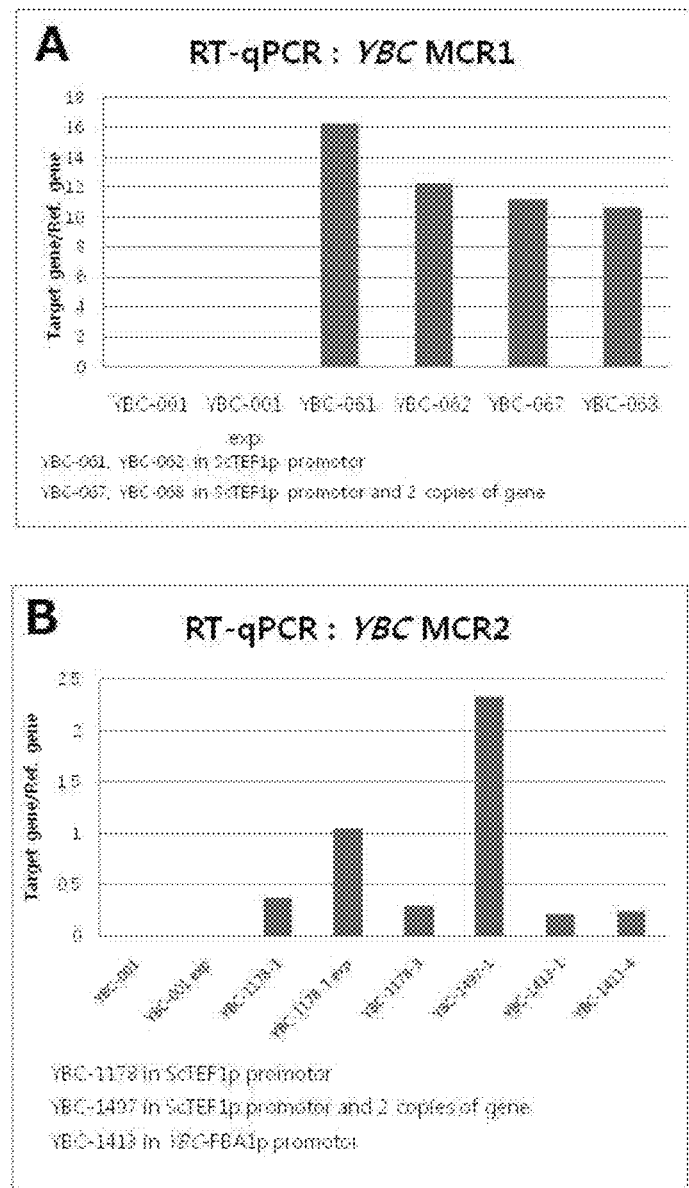

[Fig. 4]
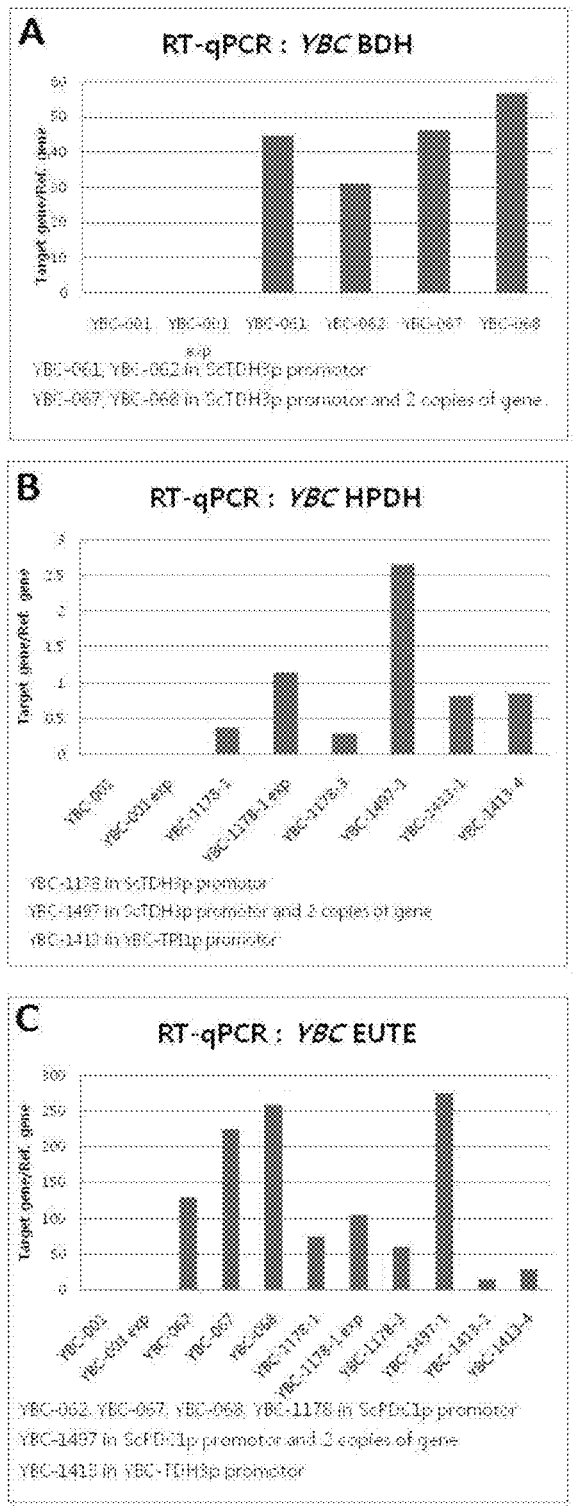

[Fig. 5]
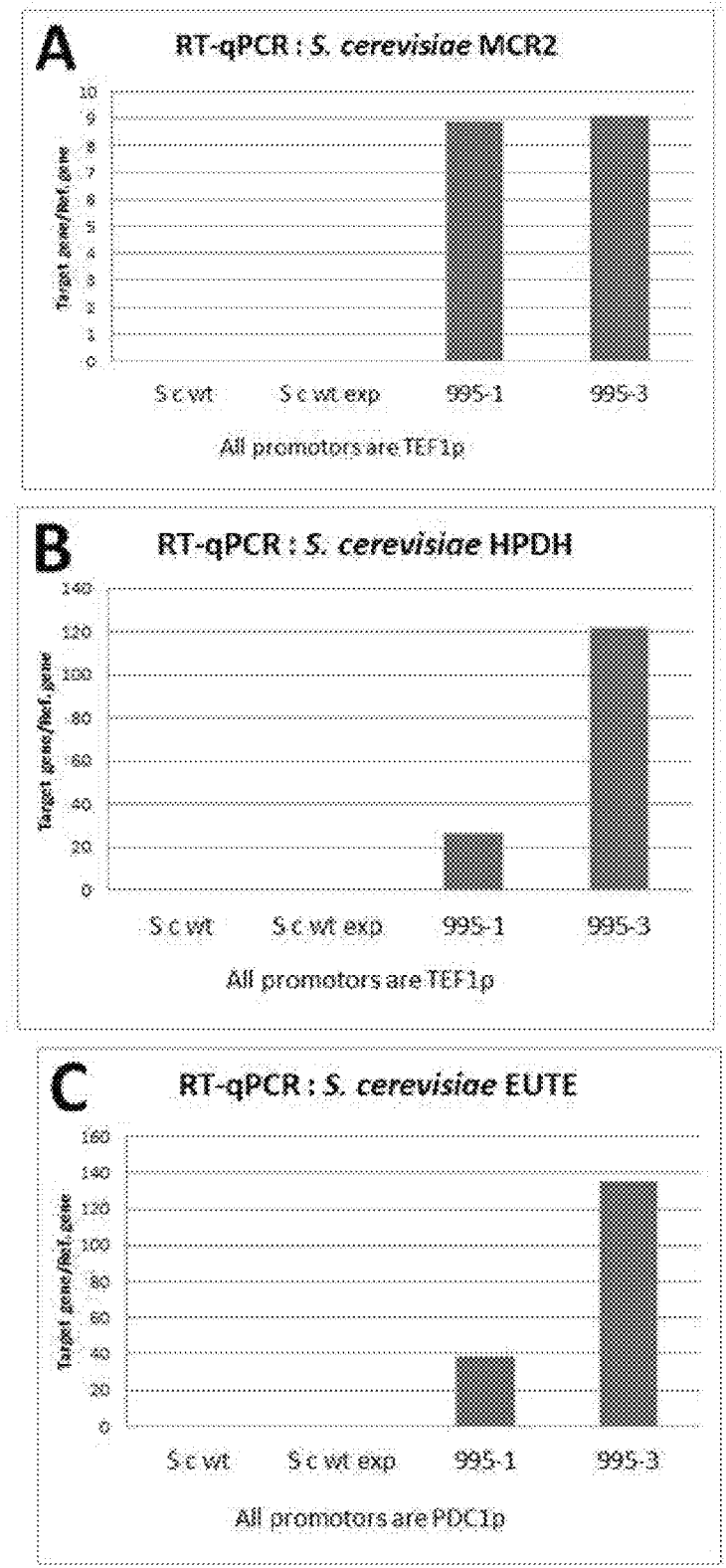

[Fig. 6]
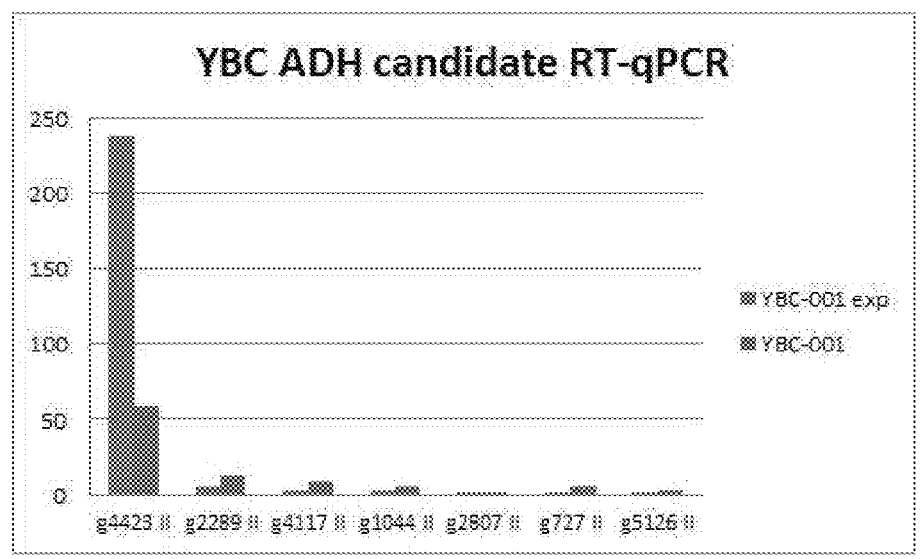

[Fig. 7]
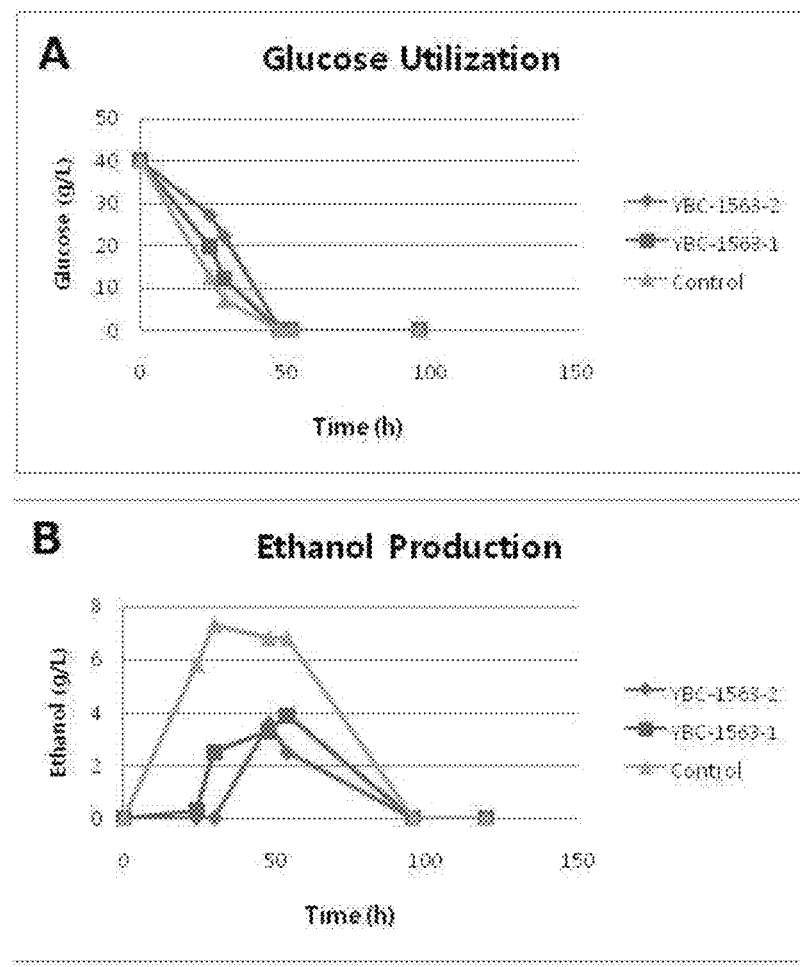

[Fig. 8]
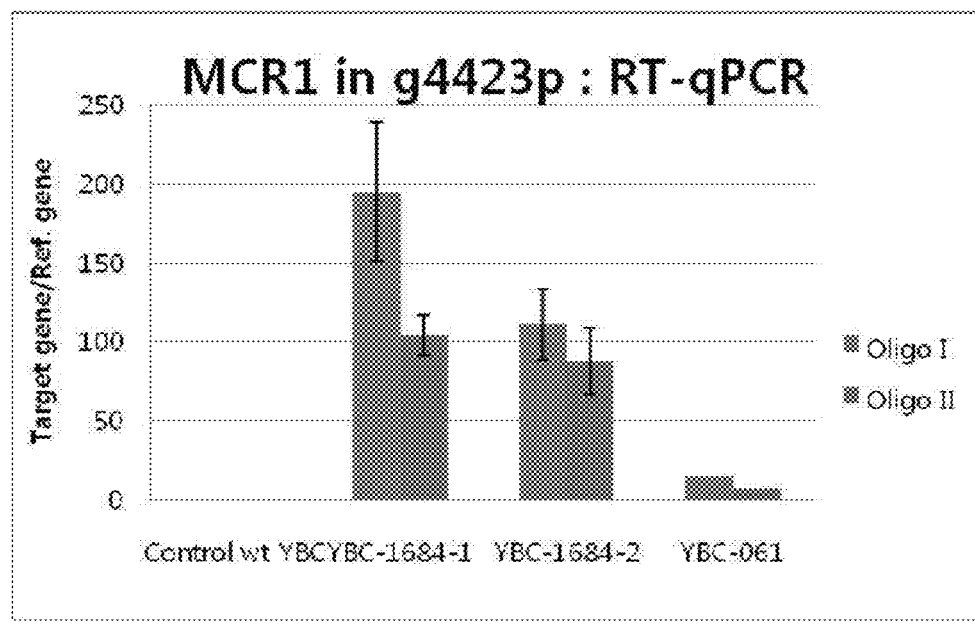
[Fig. 9]
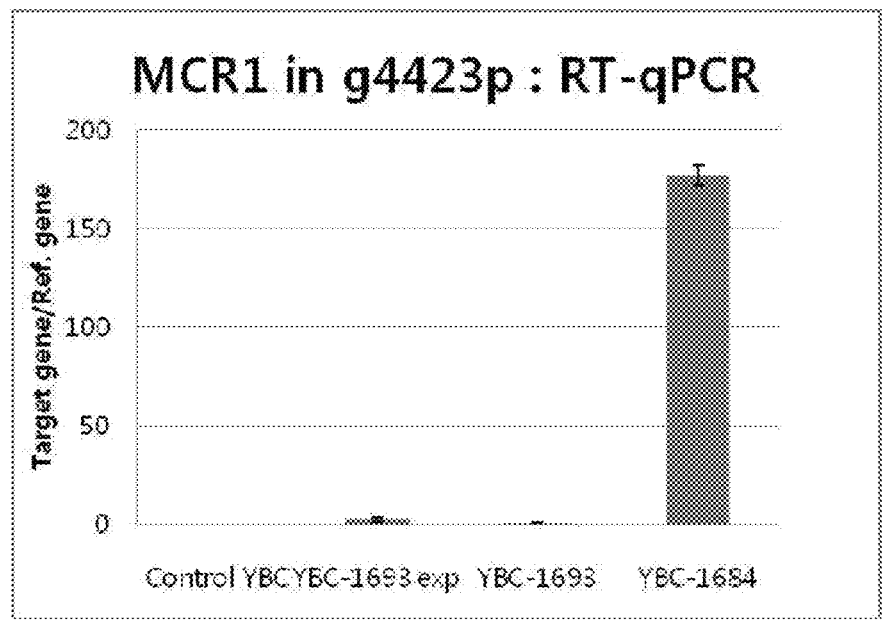

[Fig. 10]
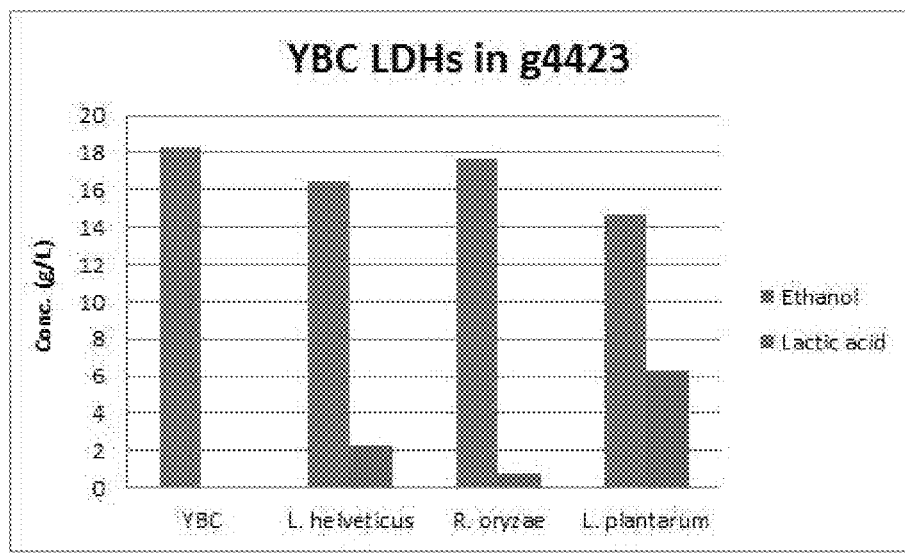

SEQUENCE LISTING

```
<160> NUMBER OF SEQ ID NOS: 81

<210> SEQ ID NO 1
<211> LENGTH: 988
<212> TYPE: DNA
<213> ORGANISM: Artificial Sequence
<220> FEATURE:
<223> OTHER INFORMATION: g4423 promotor region Allele 1

<400> SEQUENCE: 1
gttaactcag ttttctctct ttccctccac cccacgttac tctgcgaaca aaaatacgca      60
cagaatgaac atctgattga ttaatattta tatattactt agtggcaccc ctacaaacaa     120
accaattttg aatatttctc accatcatga tatttattta gggcaagaat ttcatgtaca     180
tacgtgcgtg tactgcatag ttttgttata tgtaaataac cagcaatata tcaccaatga     240
taaatgctca gtaatttatt tggaaccaaa atagtttcag taatcaaata atacaataac     300
```

-continued

```
taacaagtgc tgattataca acagctgtta acaacacaaa cacgctctct tctattctct    360
tccctgcttg ttcgtgtggt atattcccga atttgcaatt tagaaattat atttttaaa    420
agaattgttc tccatttttct ggtagtcgta agtggcaaat tggatcataa gacacaatct   480
tgttagttcg actgctaaca ccagacaaga ccgaacgaaa acagaaaaaa aagataattt    540
tgttattctg ttcaattctc tctctctttt taaggtatct ttacattaca ttacatatcc    600
caaattacaa caagagcaag aaatgaagca caacaacacg ccatctttcg tgattatttt    660
atcatttcta tatcgtaact aaattaacaa atgctatgtt tcttaatttt taatgataaa    720
tctaactgct accttaattt ctcatggaaa gtggcaaata cagaaattat atattcttat    780
tcatttttctt ataatttta tcaattacca aatatatata aatgcaatta attgattgtt    840
cctgtcacat aattttttt gtttgttacc tttattctttt atccatttag tttagttctt    900
atatctttct tttctatttc tctttttcgt ttaatctcac cgtacacata tatatccata   960
tatcaataca aataaaaatc atttaaaa                                      988
```

```
<210> SEQ ID NO 2
<211> LENGTH: 961
<212> TYPE: DNA
<213> ORGANISM: Artificial Sequence
<220> FEATURE:
<223> OTHER INFORMATION: g4423 promotor region Allele 2

<400> SEQUENCE: 2
gttaactcag ttttctctct ttccctccac cccacgttac tctgcgaaca aaaaatacgc     60
acagaatgaa catctgattg attaatattt atatattact cagtggcacc cctacaaaca    120
aaccaatttt gaatattgtt caccatcatg atatttattt agggcaagaa tttcatgtac    180
atacgtgcgt gtactgcata gttttgttat atgaaaataa ccagcaatat atcaccaatg    240
aataaattct caataattta tttggaacca aataatgcaa taactagcaa actaagtggt    300
gattatacaa cagctgttaa caacacaaac atacgctctc ttctattatc tcttccctgc    360
ttgttcgtgt ggtatattca cgaatttgca atttagaaat tatattttttt aaaagaattg    420
ttctccatttt tctggtagtc gtaagtggca aattggatca taagacacaa tcttgttagt    480
tcgactgcta acaccagaca cacgaaacg aaaacaagaa aaataatta ttctctctct     540
ttttaaggta tcttacatta catatcccaa attacaacaa gagcaagaaa tgaggcacaa    600
caacacacca tcatctttcg tgattatttt tatcatttct atcatgtaat taaattaaca    660
aatgttaagt ttattaattt ttaatgataa atctagttgc taccttaatt tctcatggaa    720
agtggcaaat actgaaatta tttaattcta cttttcatttt cttataaattt ttatcaatta    780
ccaaatatat ataaatgcaa ttaattgatt gttcctgtca cataattttt tttgtttgtt    840
accttttattc tttatccatt taatttatttt cttgtatctt tcttttctat ttctctttttc    900
tgtttaatct caccgtacac atatatatcc atatatcaat acaaataaaa atcatttaaa    960
a                                                                   961
```

```
<210> SEQ ID NO 3
<211> LENGTH: 1017
<212> TYPE: DNA
<213> ORGANISM: Artificial Sequence
<220> FEATURE:
<223> OTHER INFORMATION: g4423 terminator region Allele 1

<400> SEQUENCE: 3
taagtcattt aatttattct tttagaatat atttattttg tctttatttt tgaaatgtta     60
```

```
atagtcttt tttttactt tgaacaaaaa aagtaaaat taaactttat cttatatacg      120
cttttaaaca ttaaactcgt taacgaatta tataatgatt ttatcgaact actttatgtt   180
tttttaatag aataatcttc tttattaata taacttacta cttcttaatc ttgttgtcct   240
ccattcgaaa ctcgagtgga acattttctg agtatctctc gcgtctgttc gtaccgtttt   300
tccaatttct ttcgggaaac ggaactggac gcattttatt tgactgttga aagggagatt   360
taatatttat atagcgagat ataacaacta acttataagt ttacacaggc tgttatcaca   420
tatatatata tatatcaaca gaggactagc tcactagact aacattagat atgtcgatgc   480
tgaaccgttt gtttggtgtt agatccattt cacaatgtgc tactcgttta caacgttcta   540
cagggacaaa tatatcagaa ggtccactaa gaattattcc acaattacaa actttctatt   600
ctgctaatcc aatgcatgat aacaatatcg acaagctaga aaatcttcta cgtaaatata   660
tcaagttacc aagtacaaac aatttattga agacacatgg aatacatct acagaaattg   720 atccaacaaa attattacaa tcacaaaatt cttcacgtcc tttatggtta tcattcaagg   780
attatacagt gattggaggt ggttcacgtt taaaacctac tcaatacacg gaactttat   840 ttctattgaa taaactacat agtatcgatc cacaattaat gaatgatgat attaagaacg   900
aattagctca ttattataag aatacttcac aggaaactaa taaagtcacc atccctaaat   960
tggatgaatt cggtagaagt attggaatcg gtagaaggaa atccgcaact gcaaaag      1017
```

<210> SEQ ID NO 4
<211> LENGTH: 1018
<212> TYPE: DNA
<213> ORGANISM: Artificial Sequence
<220> FEATURE:
<223> OTHER INFORMATION: g4423 terminator region Allele 2

<400> SEQUENCE: 4

```
taagtcattt aatttattct tttagaatat atttattttg tctttatttt tgaaatgtta     60 atagtcttt ttttacttg aaaaaaaaa aagtaaaat taaacttatc ttatatacgc       120
ttttaaacat taaactcgtt aacgaattat ataatgattt tatcgaacta ctttatgttt   180
ttttaataga ataatcttct ttattaatat aacttactac ttcttaatct tgttgtcctc   240
cattcgaaac tcgagaggaa caattttctga gtctctctcg cacccttttcg tacgtaccgt   300 ttttccaatt tctttcggga acggaactg acgcattttt atttgactgt tgaaagggag    360
atttaatatt tatatagaga gataacaa ctaacttata agtttataca ggctgttatc    420
acatatatat atatatcaac agaggactag ctcaatagaa taacattaga tatgtcgatg   480
ctgaaccgtt tgtttggtgt tagatccatt tcacaatgtg ctactcgttt acaacgttct   540
acagggacaa atatatcaga aggtccacta agaattattc cacaattaca aactttctat   600
tctgctaatc caatgcatga taacaatatc gacaagctag aaaatcttct acgtaaatat   660
atcaagttac caagtacaaa taacttattg aagacacatg gaatacatc tacagaaatc   720 gatccaacaa aattattaca atcacaaaat tcttcacgtc ctttatggtt atcattcaag   780
gattatacag tgattggagg tggttcacgt ttaaaaccta ctcaatacac agaactttta   840
tttctattga ataaactaca tagtatcgat ccacaattaa tgaatgatga tattaagaac   900
gaattagctc attattataa gaatacttca caggaaacta ataaagtcac catccctaaa   960
ttggatgaat tcggtagaag tattggaatc ggtagaagga atccgcaac tgcaaaag    1018
```

<210> SEQ ID NO 5

<211> LENGTH: 6402
<212> TYPE: DNA
<213> ORGANISM: Artificial Sequence
<220> FEATURE:
<223> OTHER INFORMATION: g4423 deletion cassette containing plasmid Allele 1

<400> SEQUENCE: 5

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat tgcctgcagg     660
gttaactcag ttttctctct ttccctccac cccacgttac tctgcgaaca aaaatacgca     720
cagaatgaac atctgattga ttaatattta tatattactt agtggcaccc ctacaaacaa     780
accaattttg aatatttctc accatcatga tatttattta gggcaagaat tcatgtaca     840
tacgtgcgtg tactgcatag ttttgttata tgtaaataac cagcaatata tcaccaatga     900
taaatgctca gtaatttatt tggaaccaaa atagtttcag taatcaaata atacaataac     960
taacaagtgc tgattataca acagctgtta acaacacaaa cacgctctct tctattctct    1020
tccctgcttg ttcgtgtggt atattcccga atttgcaatt tagaaattat atttttaaa    1080
agaattgttc tccattttct ggtagtcgta agtggcaaat tggatcataa gacacaatct    1140
tgttagttcg actgctaaca ccagacaaga ccgaacgaaa acagaaaaaa aagataattt    1200
tgttattctg ttcaattctc tctctctttt taaggtatct ttacattaca ttacatatcc    1260
caaattacaa caagagcaag aaatgaagca caacaacacg ccatctttcg tgattatttt    1320
atcatttcta tatcgtaact aaattaacaa atgctatgtt tcttaatttt taatgataaa    1380
tctaactgct accttaattt ctcatggaaa gtggcaaata cagaaattat atattcttat    1440
tcatttttctt ataattttta tcaattacca aatatatata aatgcaatta attgattgtt    1500
cctgtcacat aattttttt gtttgttacc tttattcttt atccatttag tttagttctt    1560
atatctttct tttctatttc tcttttttcgt ttaatctcac cgtacacata tatatccata    1620
tatcaataca aataaaaatc atttaaaagg gcccacgtcc gagggagctc tagtacctcg    1680
taccgttcgt ataatgtatg ctatacgaag ttatcatcca ggattctgtt tagcttgcct    1740
cgtccccgcc gggtcacccg gccagcgaca tggaggccca gaataccctc cttgacagtc    1800
ttgacgtgcg cagctcaggg gcatgatgtg actgtcgccc gtacatttag cccatacatc    1860
cccatgtata atcatttgca tccatacatt ttgatggccg cacggcgcga agcaaaaatt    1920
acggctcctc gctgcagacc tgcgagcagg gaaacgctcc cctcacagac gcgttgaatt    1980
gtccccacgc cgcgccctg tagagaaata taaaaggtta ggatttgcca ctgaggttct    2040
tctttcatat acttcctttt aaaatcttgc taggatacag ttctcacatc acatccgaac    2100
```

-continued

```
ataaacaacc atgggtaagg aaaagactca cgtttcgagg ccgcgattaa attccaacat    2160
ggatgctgat ttatatgggt ataaatgggc tcgcgataat gtcgggcaat caggtgcgac    2220
aatctatcga ttgtatggga agcccgatgc gccagagttg tttctgaaac atggcaaagg    2280
tagcgttgcc aatgatgtta cagatgagat ggtcagacta aactggctga cggaatttat    2340
gcctcttccg accatcaagc atttttatccg tactcctgat gatgcatggt tactcaccac    2400
tgcgatcccc ggcaaaacag cattccaggt attagaagaa tatcctgatt caggtgaaaa    2460
tattgttgat gcgctggcag tgttcctgcg ccggttgcat tcgattcctg tttgtaattg    2520
tccttttaac agtgatcgcg tatttcgtct cgctcaggcg caatcacgaa tgaataacgg    2580
tttggttgat gcgagtgatt ttgatgacga gcgtaatggc tggcctgttg aacaagtctg    2640
gaaagaaatg cataagcttt tgccattctc accggattca gtcgtcactc atggtgattt    2700
ctcacttgat aaccttattt tgacgagggg aaattaata ggttgtattg atgttggacg    2760
agtcggaatc gcagaccgat accaggatct tgccatccta tggaactgcc tcggtgagtt    2820
ttctccttca ttacagaaac ggcttttcca aaaatatggt attgataatc ctgatatgaa    2880
taaattgcag tttcatttga tgctcgatga gttttctaa tcagtactga caataaaaag    2940
attcttgttt tcaagaactt gtcatttgta tagtttttt atattgtagt tgttctattt    3000
taatcaaatg ttagcgtgat ttatattttt tttcgcctcg acatcatctg cccagatgcg    3060
aagttaagtg cgcagaaagt aatatcatgc gtcaatcgta tgtgaatgct ggtcgctata    3120
ctgctgtcga ttcgatacta acgccgccat ccagtgtcga aaagtatcag caaataactt    3180
cgtataatgt atgctatacg aacggtagcg atcgctttgt ctttatttt gaatgttaa    3240 tagtctttt tttttacttt gaacaaaaaa agtaaaatt aaaacttatc ttatatacgc    3300
ttttaaacat taaactcgtt aacgaattat ataatgattt tatcgaacta ctttatgttt    3360
ttttaataga ataatcttct ttattaatat aacttactac ttcttaatct tgttgtcctc    3420
cattcgaaac tcgagtggaa cattttctga gtatctctcg cgtctgttcg taccgttttt    3480
ccaatttctt tcgggaaacg gaactggacg cattttattt gactgttgaa agggagattt    3540
aatatttata tagcgagata taacaactaa cttataagtt tacacaggct gttatcacat    3600
atatatatat atatcaacag aggactagct cactagacta acattagata tgtcgatgct    3660
gaaccgtttg tttggtgtta gatccatttc acaatgtgct actcgtttac aacgttctac    3720
agggacaaat atatcagaag gtccactaag aattattcca caattacaaa ctttctattc    3780
tgctaatcca atgcatgata acaatatcga caagctagaa atcttctac gtaaatatat    3840 caagttacca agtacaaaca atttattgaa gacacatggg aatacatcta cagaaattga    3900
tccaacaaaa ttattacaat cacaaaattc ttcacgtcct ttatggttat cattcaagga    3960
ttatacagtg attggaggtg gttcacgttt aaaacctact caatacacgg aacttttatt    4020
tctattgaat aaactacata gtatcgatcc acaattaatg aatgatgata ttaagaacga    4080
attagctcat tattataaga atacttcaca ggaaactaat aaagtcacca tccctaaatt    4140
ggatgaattc ggtagaagta ttggaatcgg tagaaggaaa tccgcaactg caaagggcg    4200 cgcccagctt ttgttcccct tagtgagggt taatttcgag cttggcgtaa tcatggtcat    4260
agctgtttcc tgtgtgaaat tgttatccgc tcacaattcc acacaacata cgagccggaa    4320
gcataaagtg taaagcctgg ggtgcctaat gagtgagcta actcacatta attgcgttgc    4380
gctcactgcc cgctttccag tcgggaaacc tgtcgtgcca gctgcattaa tgaatcggcc    4440
aacgcgcggg gagaggcggt ttgcgtattg ggcgctcttc cgcttcctcg ctcactgact    4500
```

```
cgctgcgctc ggtcgttcgg ctgcggcgag cggtatcagc tcactcaaag gcggtaatac      4560
ggttatccac agaatcaggg gataacgcag gaaagaacat gtgagcaaaa ggccagcaaa      4620
aggccaggaa ccgtaaaaag gccgcgttgc tggcgttttt ccataggctc cgcccccctg      4680
acgagcatca caaaaatcga cgctcaagtc agaggtggcg aaacccgaca ggactataaa      4740
gataccaggc gtttccccct ggaagctccc tcgtgcgctc tcctgttccg accctgccgc      4800
ttaccggata cctgtccgcc tttctccctt cgggaagcgt ggcgctttct catagctcac      4860
gctgtaggta tctcagttcg gtgtaggtcg ttcgctccaa gctgggctgt gtgcacgaac      4920
cccccgttca gcccgaccgc tgcgccttat ccggtaacta tcgtcttgag tccaacccgg      4980
taagacacga cttatcgcca ctggcagcag ccactggtaa caggattagc agagcgaggt      5040
atgtaggcgg tgctacagag ttcttgaagt ggtggcctaa ctacggctac actagaagga      5100
cagtatttgg tatctgcgct ctgctgaagc cagttacctt cggaaaaaga gttggtagct      5160
cttgatccgg caaacaaacc accgctggta gcggtggttt ttttgtttgc aagcagcaga      5220
ttacgcgcag aaaaaaagga tctcaagaag atcctttgat cttttctacg ggtctgacg      5280 ctcagtggaa cgaaaactca cgttaaggga ttttggtcat gagattatca aaaaggatct      5340
tcacctagat ccttttaaat taaaaatgaa gttttaaatc aatctaaagt atatatgagt      5400
aaacttggtc tgacagttac caatgcttaa tcagtgaggc acctatctca gcgatctgtc      5460
tatttcgttc atccatagtt gcctgactcc ccgtcgtgta gataactacg atacgggagg      5520
gcttaccatc tggccccagt gctgcaatga taccgcgaga cccacgctca ccggctccag      5580
atttatcagc aataaaccag ccagccggaa gggccgagcg cagaagtggt cctgcaactt      5640
tatccgcctc catccagtct attaattgtt gccgggaagc tagagtaagt agttcgccag      5700
ttaatagttt gcgcaacgtt gttgccattg ctacaggcat cgtggtgtca cgctcgtcgt      5760
ttggtatggc ttcattcagc tccggttccc aacgatcaag gcgagttaca tgatccccca      5820
tgttgtgcaa aaaagcggtt agctccttcg gtcctccgat cgttgtcaga agtaagttgg      5880
ccgcagtgtt atcactcatg gttatggcag cactgcataa ttctcttact gtcatgccat      5940
ccgtaagatg cttttctgtg actggtgagt actcaaccaa gtcattctga aatagtgta      6000 tgcggcgacc gagttgctct tgcccggcgt caatacggga taataccgcg ccacatagca      6060
gaactttaaa agtgctcatc attggaaaac gttcttcggg gcgaaaactc tcaaggatct      6120
taccgctgtt gagatccagt tcgatgtaac ccactcgtgc acccaactga tcttcagcat      6180
cttttacttt caccagcgtt tctgggtgag caaaaacagg aaggcaaaat gccgcaaaaa      6240
agggaataag ggcgacacgg aaatgttgaa tactcatact cttcctttt caatattatt      6300 gaagcattta tcagggttat tgtctcatga gcggatacat atttgaatgt atttagaaaa      6360
ataaacaaat aggggttccg cgcacatttc cccgaaaagt gc                         6402
```

<210> SEQ ID NO 6
<211> LENGTH: 6376
<212> TYPE: DNA
<213> ORGANISM: Artificial Sequence
<220> FEATURE:
<223> OTHER INFORMATION: g4423 deletion cassette containing plasmid
      Allele 2

<400> SEQUENCE: 6

```
cacctgacgc gccctgtagc ggcgcattaa gcgcggcggg tgtggtggtt acgcgcagcg       60
tgaccgctac acttgccagc gccctagcgc ccgctccttt cgctttcttc ccttcctttc      120
```

```
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240
gtgggccatc gccctgatag acggtttttc gcccttttgac gttggagtcc acgttcttta   300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540 aggggggatgt gctgcaaggc gattaagttg gtaacgcca gggttttccc agtcacgacg    600
ttgtaaaacg acggccagtg aattgtaata cgactcacta tagggcgaat tgcctgcagg    660
gttaactcag ttttctctct ttccctccac cccacgttac tctgcgaaca aaaaatacgc    720
acagaatgaa catctgattg attaatattt atatattact cagtggcacc cctacaaaca    780
aaccaatttt gaatattgtt caccatcatg atatttattt agggcaagaa tttcatgtac    840
atacgtgcgt gtactgcata gttttgttat atgaaaataa ccagcaatat atcaccaatg    900
aataaattct caataattta tttggaacca aataatgcaa taactagcaa actaagtggt    960
gattatacaa cagctgttaa caacacaaac atacgctctc ttctattatc tcttccctgc   1020
ttgttcgtgt ggtatattca cgaatttgca atttagaaat tatatttttt aaaagaattg   1080
ttctccattt tctggtagtc gtaagtggca aattggatca taagacacaa tcttgttagt   1140
tcgactgcta acaccagaca acaccgaacg aaaacaagaa aaaataatta ttctctctct   1200
ttttaaggta tcttacatta catatcccaa attacaacaa gagcaagaaa tgaggcacaa   1260
caacacacca tcatctttcg tgattatttt tatcatttct atcatgtaat taaattaaca   1320
aatgttaagt ttattaattt ttaatgataa atctagttgc taccttaatt tctcatggaa   1380
agtggcaaat actgaaatta tttaattcta cttttcatttt cttataattt ttatcaatta   1440
ccaaatatat ataaatgcaa ttaattgatt gttcctgtca cataatttttt tttgtttgtt   1500 accttttattc tttatccatt taatttattt cttgtatctt tcttttctat ttctcttttc   1560
tgtttaatct caccgtacac atatatatcc atatatcaat acaaataaaa atcatttaaa   1620
agggcccacg tccgagggag ctctagtacc tcgtaccgtt cgtataatgt atgctatacg   1680
aagttatcat ccaggattct gtttagcttg cctcgtcccc gccgggtcac ccggccagcg   1740
acatggaggc ccagaatacc ctccttgaca gtcttgacgt gcgcagctca ggggcatgat   1800
gtgactgtcg cccgtacatt tagcccatac atccccatgt ataatcattt gcatccatac   1860
attttgatgg ccgcacggcg cgaagcaaaa attacggctc ctcgctgcag acctgcgagc   1920
agggaaacgc tcccctcaca gacgcgttga attgtcccca cgccgcgccc ctgtagagaa   1980
atataaaagg ttaggatttg ccactgaggt tcttctttca tatacttcct tttaaaatct   2040
tgctaggata cagttctcac atcacatccg aacataaaca accatgggta aggaaaagac   2100
tcacgtttcg aggccgcgat taaattccaa catggatgct gatttatatg gtataaatg    2160 ggctcgcgat aatgtcgggc aatcaggtgc gacaatctat cgattgtatg ggaagcccga   2220
tgcgccagag ttgtttctga acatggcaa aggtagcgtt gccaatgatg ttacagatga    2280
gatggtcaga ctaaactggc tgacggaatt tatgcctctt ccgaccatca agcattttat   2340
ccgtactcct gatgatgcat ggttactcac cactgcgatc cccggcaaaa cagcattcca   2400
ggtattagaa gaatatcctg attcaggtga aaatattgtt gatgcgctgg cagtgttcct   2460
```

```
gcgccggttg cattcgattc ctgtttgtaa ttgtccttt  aacagtgatc gcgtatttcg   2520
tctcgctcag gcgcaatcac gaatgaataa cggtttggtt gatgcgagtg attttgatga   2580
cgagcgtaat ggctggcctg ttgaacaagt ctggaaagaa atgcataagc ttttgccatt   2640
ctcaccggat tcagtcgtca ctcatggtga tttctcactt gataaccta  ttttgacga    2700
ggggaaatta ataggttgta ttgatgttgg acgagtcgga atcgcagacc gataccagga   2760
tcttgccatc ctatggaact gcctcggtga gttttctcct tcattacaga acggcttt     2820
tcaaaaatat ggtattgata atcctgatat gaataaattg cagtttcatt tgatgctcga   2880
tgagttttc  taatcagtac tgacaataaa aagattcttg ttttcaagaa cttgtcattt    2940
gtatagtttt tttatattgt agttgttcta ttttaatcaa atgttagcgt gatttatatt   3000
ttttttcgcc tcgacatcat ctgcccagat gcgaagttaa gtgcgcagaa agtaatatca   3060
tgcgtcaatc gtatgtgaat gctggtcgct atactgctgt cgattcgata ctaacgccgc   3120
catccagtgt cgaaaagtat cagcaaataa cttcgtataa tgtatgctat acgaacggta   3180
gcgatcgctt tgtctttatt tttgaaatgt taatagtctt ttttttactt tgaaaaaaaa   3240
aaaaagtaaa attaaactta tcttatatac gcttttaaac attaaactcg ttaacgaatt   3300
atataatgat tttatcgaac tactttatgt ttttttaata gaataatctt ctttattaat   3360
ataacttact acttcttaat cttgttgtcc tccattcgaa actcgagagg aacaatttct   3420
gagtctctct cgcaccctt  cgtacgtacc gttttccaa  tttctttcgg gaaacggaac    3480
tggacgcatt ttatttgact gttgaaaggg agatttaata tttatataga gagatataac   3540
aactaactta taagtttata caggctgtta tcacatatat atatatatca acagaggact   3600
agctcaatag aataacatta gatatgtcga tgctgaaccg tttgtttggt gttagatcca   3660
tttcacaatg tgctactcgt ttacaacgtt ctacagggac aaatatatca gaaggtccac   3720
taagaattat tccacaatta caaactttct attctgctaa tccaatgcat gataacaata   3780
tcgacaagct agaaaatctt ctacgtaaat atatcaagtt accaagtaca ataacttat    3840
tgaagacaca tgggaataca tctacagaaa tcgatccaac aaaattatta caatcacaaa   3900
attcttcacg tcctttatgg ttatcattca aggattatac agtgattgga ggtggttcac   3960
gtttaaaacc tactcaatac acagaacttt tatttctatt gaataaacta catagtatcg   4020
atccacaatt aatgaatgat gatattaaga acgaattagc tcattattat aagaatactt   4080
cacaggaaac taataaagtc accatcccta aattggatga attcggtaga agtattggaa   4140
tcggtagaag gaaatccgca actgcaaaag ggcgcgccca gcttttgttc cctttagtga   4200
gggttaattt cgagcttggc gtaatcatgg tcatagctgt ttcctgtgtg aaattgttat   4260
ccgctcacaa ttccacacaa catacgagcc ggaagcataa agtgtaaagc ctggggtgcc   4320
taatgagtga gctaactcac attaattgcg ttgcgctcac tgcccgcttt ccagtcggga   4380
aacctgtcgt gccagctgca ttaatgaatc ggccaacgcg cggggagagg cggtttgcgt   4440
attgggcgct cttccgcttc ctcgctcact gactcgctgc gctcggtcgt tcggctgcgg   4500
cgagcggtat cagctcactc aaaggcggta atacggttat ccacagaatc aggggataac   4560
gcaggaaaga acatgtgagc aaaaggccag caaaaggcca ggaaccgtaa aaaggccgcg   4620
ttgctggcgt ttttccatag gctccgcccc cctgacgagc atcacaaaaa tcgacgctca   4680
agtcagaggt ggcgaaaccc gacaggacta taaagatacc aggcgtttcc ccctggaagc   4740
tccctcgtgc gctctcctgt tccgaccctg ccgcttaccg gatacctgtc cgcctttctc   4800
ccttcgggaa gcgtggcgct ttctcatagc tcacgctgta ggtatctcag ttcggtgtag   4860
```

| | |
|---|---|
| gtcgttcgct ccaagctggg ctgtgtgcac gaaccccccg ttcagcccga ccgctgcgcc | 4920 |
| ttatccggta actatcgtct tgagtccaac ccggtaagac acgacttatc gccactggca | 4980 |
| gcagccactg gtaacaggat tagcagagcg aggtatgtag gcggtgctac agagttcttg | 5040 |
| aagtggtggc ctaactacgg ctacactaga aggacagtat ttggtatctg cgctctgctg | 5100 |
| aagccagtta ccttcggaaa aagagttggt agctcttgat ccggcaaaca accaccgct | 5160 |
| ggtagcggtg gttttttgt ttgcaagcag cagattacgc gcagaaaaaa aggatctcaa | 5220 |
| gaagatcctt tgatcttttc tacggggtct gacgctcagt ggaacgaaaa ctcacgttaa | 5280 |
| gggattttgg tcatgagatt atcaaaaagg atcttcacct agatcctttt aaattaaaaa | 5340 |
| tgaagtttta aatcaatcta agtatatat gagtaaactt ggtctgacag ttaccaatgc | 5400 |
| ttaatcagtg aggcacctat ctcagcgatc tgtctatttc gttcatccat agttgcctga | 5460 |
| ctccccgtcg tgtagataac tacgatacgg gagggcttac catctggccc cagtgctgca | 5520 |
| atgataccgc gagacccacg ctcaccggct ccagatttat cagcaataaa ccagccagcc | 5580 |
| ggaagggccg agcgcagaag tggtcctgca actttatccg cctccatcca gtctattaat | 5640 |
| tgttgccggg aagctagagt aagtagttcg ccagttaata gtttgcgcaa cgttgttgcc | 5700 |
| attgctacag gcatcgtggt gtcacgctcg tcgtttggta tggcttcatt cagctccggt | 5760 |
| tcccaacgat caaggcgagt tacatgatcc cccatgttgt gcaaaaaagc ggttagctcc | 5820 |
| ttcggtcctc cgatcgttgt cagaagtaag ttggccgcag tgttatcact catggttatg | 5880 |
| gcagcactgc ataattctct tactgtcatg ccatccgtaa gatgcttttc tgtgactggt | 5940 |
| gagtactcaa ccaagtcatt ctgagaatag tgtatgcggc gaccgagttg ctcttgcccg | 6000 |
| gcgtcaatac gggataatac cgcgccacat agcagaactt taaaagtgct catcattgga | 6060 |
| aaacgttctt cggggcgaaa actctcaagg atcttaccgc tgttgagatc cagttcgatg | 6120 |
| taacccactc gtgcacccaa ctgatcttca gcatctttta ctttcaccag cgtttctggg | 6180 |
| tgagcaaaaa caggaaggca aaatgccgca aaaaagggaa taagggcgac acggaaatgt | 6240 |
| tgaatactca tactcttcct ttttcaatat tattgaagca tttatcaggg ttattgtctc | 6300 |
| atgagcggat acatatttga atgtatttag aaaaataaac aaataggggt tccgcgcaca | 6360 |
| tttccccgaa aagtgc | 6376 |

<210> SEQ ID NO 7
<211> LENGTH: 5942
<212> TYPE: DNA
<213> ORGANISM: Artificial Sequence
<220> FEATURE:
<223> OTHER INFORMATION: pSK863

<400> SEQUENCE: 7

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |

```
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgcctgcagg    660
gttaactcag ttttctctct ttccctccac cccacgttac tctgcgaaca aaaatacgca    720
cagaatgaac atctgattga ttaatatttta tatattactt agtggcaccc ctacaaacaa    780
accaattttg aatatttctc accatcatga tatttattta gggcaagaat tcatgtaca     840 tacgtgcgtg tactgcatag ttttgttata tgtaaataac cagcaatata tcaccaatga    900
taaatgctca gtaatttatt tggaaccaaa atagtttcag taatcaaata atacaataac    960
taacaagtgc tgattataca acagctgtta acaacacaaa cacgctctct tctattctct   1020
tccctgcttg ttcgtgtggt atattcccga atttgcaatt tagaaattat atttttttaaa  1080 agaattgttc tccattttct ggtagtcgta agtggcaaat tggatcataa gacacaatct   1140
tgttagttcg actgctaaca ccagacaaga ccgaacgaaa acagaaaaaa aagataattt   1200
tgttattctg ttcaattctc tctctctttt taaggtatct ttacattaca ttacatatcc   1260
caaattacaa caagagcaag aaatgaagca caacaacacg ccatctttcg tgattatttt   1320
atcatttcta tatcgtaact aaaattaacaa atgctatgtt tcttaatttt taatgataaa   1380
tctaactgct accttaattt ctcatggaaa gtggcaaata cagaaattat atattcttat   1440
tcattttctt ataattttta tcaattacca aatatatata aatgcaatta attgattgtt   1500
cctgtcacat aatttttttt gtttgttacc tttattcttt atccatttag tttagttctt   1560
atatctttct tttctatttc tcttttttcgt ttaatctcac cgtacacata tatatccata   1620
tatcaataca aataaaaatc atttaaaaat gagaagaact ttgaaggctg ccattttagg   1680
tgctacaggt ttagtcggta ttgaatacgt cagaatgtta tcacaacacc catatattaa   1740
acctgcttat ttggctggta aaggttctgt tggtaaagct tactcagaag ttgtcagatg   1800
gcaaacagtt ggtcaagtcc caaggaagt agccgatatg ccagttttgc ctaccgacgt    1860
caatgaaatc aaaaaggctg gtgtagatat tgttttctct ccattacctc aaggtgctgc   1920
aggtccagtt gaagaagaat ttgcaaaagc cggtttccct gtcatttcta attcaccaga   1980
tcatagattc gatccagacg taccttgat gataccgaa gttaacggtc acactgcatc     2040
cttaattgat gaacaaaaga aaagaagaga ctggagtggt tttattgtta ctacaccatt   2100
gtgtacagca caaggtattg ccataccatt agctcctatc tatagagatt tcagagttga   2160
ttctgtattc ataaccacta tgcaatcctt gagtggtgaa ggttatcctg tgttgcttc    2220 attggatgta gttgacaaca tcaaggtttt gggtgacgct tacgacgcta aaactgttaa   2280
ggaagtcaca agaattttat ctgaagttaa gagaaacgtc ccaggtacta tggatgaatt   2340
gactttatca gcaacaaccc atagaatagc caccattcat ggtcactacg aagtaatgta   2400
cgttactttt aaagaagatg tcaaggtaga aaaggttaag gaaactttgg ctaacttcaa   2460
aggtgaacct caagatatga gttaccaac agcaccttcc agaccaatct tgattaccga    2520
attagataac agaccacaac cttacttcga tagatgggca ggtgacgttc caggtatgtc   2580
cgtcgtagtt ggtagattaa agcaagttaa caacagaact gttagattgg tttcttttgat  2640 ccataacaca gtcagaggtg ccgctggtgg tggtattttg gtagccgaat atttgatcga   2700
aaagggttac atccctaagt gagtcattta atttattctt ttagaatata attattttgt   2760
ctttattttt gaaatgttaa tagtcttttt tttttacttt gaacaaaaaa aagtaaaatt   2820
aaaacttatc ttatatacgc ttttaaacat taaactcgtt aacgaattat ataatgattt   2880
```

```
tatcgaacta ctttatgttt ttttaataga ataatcttct ttattaatat aacttactac    2940
ttcttaatct tgttgtcctc cattcgaaac tcgagtggaa cattttctga gtatctctcg    3000
cgtctgttcg taccgttttt ccaatttctt tcgggaaacg gaactggacg cattttattt    3060
gactgttgaa agggagattt aatatttata tagcgagata taacaactaa cttataagtt    3120
tacacaggct gttatcacat atatatatat atcaacag aggactagct cactagacta     3180
acattagata tgtcgatgct gaaccgtttg tttggtgtta gatccatttc acaatgtgct    3240
actcgtttac aacgttctac agggacaaat atatcagaag gtccactaag aattattcca    3300
caattacaaa ctttctattc tgctaatcca atgcatgata acaatatcga caagctagaa    3360
aatcttctac gtaaatatat caagttacca agtacaaaca atttattgaa gacacatggg    3420
aatacatcta cagaaattga tccaacaaaa ttattacaat cacaaaattc ttcacgtcct    3480
ttatggttat cattcaagga ttatacagtg attggaggtg gttcacgttt aaaacctact    3540
caatacacgg aacttttatt tctattgaat aaactacata gtatcgatcc acaattaatg    3600
aatgatgata ttaagaacga attagctcat tattataaga atacttcaca ggaaactaat    3660
aaagtcacca tccctaaatt ggatgaattc ggtagaagta ttggaatcgg tagaaggaaa    3720
tccgcaactg caaaagggcg cgcccagctt ttgttcccctt tagtgagggt taatttcgag    3780
cttggcgtaa tcatggtcat agctgttttcc tgtgtgaaat tgttatccgc tcacaattcc    3840
acacaacata cgagccggaa gcataaagtg taaagcctgg ggtgcctaat gagtgagcta    3900
actcacatta ttgcgttgc gctcactgcc cgctttccag tcgggaaacc tgtcgtgcca    3960
gctgcattaa tgaatcggcc aacgcgcggg gagaggcggt ttgcgtattg ggcgctcttc    4020
cgcttcctcg ctcactgact cgctgcgctc ggtcgttcgg ctgcggcgag cggtatcagc    4080
tcactcaaag gcggtaatac ggttatccac agaatcaggg gataacgcag gaaagaacat    4140
gtgagcaaaa ggccagcaaa aggccaggaa ccgtaaaaag gccgcgttgc tggcgttttt    4200
ccataggctc cgcccccctg acgagcatca caaaaatcga cgctcaagtc agaggtggcg    4260
aaacccgaca ggactataaa gataccaggc gtttccccct ggaagctccc tcgtgcgctc    4320
tcctgttccg accctgccgc ttaccggata cctgtccgcc tttctccctt cgggaagcgt    4380
ggcgctttct catagctcac gctgtaggta tctcagttcg gtgtaggtcg ttcgctccaa    4440
gctgggctgt gtgcacgaac ccccgttca gcccgaccgc tgcgcctat ccggtaacta    4500 tcgtcttgag tccaacccgg taagacacga cttatcgcca ctggcagcag ccactggtaa    4560
caggattagc agagcgaggt atgtaggcgg tgctacagag ttcttgaagt ggtggcctaa    4620
ctacggctac actagaagga cagtatttgg tatctgcgct ctgctgaagc cagttacctt    4680
cggaaaaaga gttggtagct cttgatccgg caaacaaacc accgctggta gcggtggttt    4740
ttttgtttgc aagcagcaga ttacgcgcag aaaaaaagga tctcaagaag atcctttgat    4800
cttttctacg gggtctgacg ctcagtggaa cgaaaactca cgttaaggga ttttggtcat    4860
gagattatca aaaaggatct tcacctagat ccttttaaat taaaaatgaa gttttaaatc    4920
aatctaaagt atatatgagt aaacttggtc tgacagttac caatgcttaa tcagtgaggc    4980
acctatctca gcgatctgtc tatttcgttc atccatagtt gcctgactcc ccgtcgtgta    5040
gataactacg atacgggagg gcttaccatc tggccccagt gctgcaatga taccgcgaga    5100
cccacgctca ccggctccag atttatcagc aataaaccag ccagccggaa gggccgagcg    5160
cagaagtggt cctgcaactt tatccgcctc catccagtct attaattgtt gccgggaagc    5220
```

```
tagagtaagt agttcgccag ttaatagttt gcgcaacgtt gttgccattg ctacaggcat    5280
cgtggtgtca cgctcgtcgt ttggtatggc ttcattcagc tccggttccc aacgatcaag    5340
gcgagttaca tgatccccca tgttgtgcaa aaaagcggtt agctccttcg gtcctccgat    5400
cgttgtcaga agtaagttgg ccgcagtgtt atcactcatg gttatggcag cactgcataa    5460
ttctcttact gtcatgccat ccgtaagatg ctttctgtg actggtgagt actcaaccaa     5520
gtcattctga gaatagtgta tgcggcgacc gagttgctct tgcccggcgt caatacggga    5580
taataccgcg ccacatagca gaactttaaa agtgctcatc attggaaaac gttcttcggg    5640
gcgaaaactc tcaaggatct taccgctgtt gagatccagt tcgatgtaac ccactcgtgc    5700
acccaactga tcttcagcat cttttacttt caccagcgtt tctgggtgag caaaaacagg    5760
aaggcaaaat gccgcaaaaa agggaataag ggcgacacgg aaatgttgaa tactcatact    5820 cttcctttt caatattatt gaagcattta tcagggttat tgtctcatga gcggatacat    5880
atttgaatgt atttagaaaa ataaacaaat aggggttccg cgcacatttc cccgaaaagt    5940
gc                                                                   5942

<210> SEQ ID NO 8
<211> LENGTH: 11693
<212> TYPE: DNA
<213> ORGANISM: Artificial Sequence
<220> FEATURE:
<223> OTHER INFORMATION: pSK-865

<400> SEQUENCE: 8
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctccct ttagggttcc      180 gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gatttttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgcctgcagg    660
agagttacgt gatcagaatg ggaaattatt accacctcca cctggattcg aattcagcac    720
ttcctttgaa tcgaagctaa caccagagga gataaatatg aattctttac caatggaacc    780
acctaattat tcagataatg aaagtacata tgcatttaaa tttcatccaa gagattcatt    840
atcaagcaat acaggtagaa ccatcccaat tgtaggaagt agcaaaagat tagacaatag    900
gatcctggta ggaagtagca gcaaccgttt aaggaattcc ccagatgata aagacgacta    960
cgatttcgat gatgacgacg attgcgacta cgatgaatat gatatccccg aggatgatga   1020
tgacgacaac aacgataata tccatgatat ccacgatatc gagaccgatg aagacgacga   1080
agagatcaca gatgaaatgg cacacatgat ctcccatcag tgatcttata taaatataca   1140
agataatata tatatatatg taacatctaa agacagatac ccgatcgtct tccttattct   1200
tccaaaggac tctgaagttg gcccgaaatt agcaccgaaa tcgggaacaa ccaacacggc   1260
gacacccgtg gagcgactgc gcgggaaaca ggagtggcct gacagacagc gacaacaata   1320
```

```
tgccatttct gcgtatcgga gtcgtcgttg atagcggggg gtgggcagac agaaagagaa    1380
aagcgggcga catcaattcc ggcggtggag gggggagtca tcccatgttt tgtcattatt    1440
attatataaa gtagatatga ctgataaaga tttgttgggt atgcttttt  gaactaactt    1500 ataaacatat tatatattac aacacggttc aatataacaa ggactgttga gtgagataac    1560
attaaattcg ggcccgttaa ctcagttttc tctctttccc tccaccccac gttactctgc    1620
gaacaaaaat acgcacagaa tgaacatctg attgattaat atttatatat tacttagtgg    1680 caccccctaca aacaaaccaa ttttgaatat ttctcaccat catgatattt atttagggca    1740
agaatttcat gtacatacgt gcgtgtactg catagttttg ttatatgtaa ataaccagca    1800
atatatcacc aatgataaat gctcagtaat ttatttggaa ccaaaatagt ttcagtaatc    1860
aaataataca ataactaaca agtgctgatt atacaacagc tgttaacaac acaaacacgc    1920
tctcttctat tctcttccct gcttgttcgt gtggtatatt cccgaatttg caatttagaa    1980
attatatttt ttaaaagaat tgttctccat tttctggtag tcgtaagtgg caaattggat    2040
cataagacac aatcttgtta gttcgactgc taacaccaga caagaccgaa cgaaaacaga    2100
aaaaaaagat aattttgtta ttctgttcaa ttctctctct ctttttaagg tatctttaca    2160
ttacattaca tatcccaaat tacaacaaga gcaagaaatg aagcacaaca acacgccatc    2220
tttcgtgatt attttatcat ttctatatcg taactaaatt aacaaatgct atgtttctta    2280 attttttaatg ataaatctaa ctgctacctt aatttctcat ggaaagtggc aaatacagaa    2340
attatatatt cttattcatt ttcttataat ttttatcaat taccaaatat atataaatgc    2400
aattaattga ttgttcctgt cacataattt tttttgtttg ttacctttat tctttatcca    2460
tttagtttag ttcttatatc tttcttttct atttctcttt ttcgtttaat ctcaccgtac    2520
acatatatat ccatatatca atacaaataa aaatcattta aaagtcgaca acaaaatgag    2580
aagaactttg aaggctgcca ttttaggtgc tacaggttta gtcggtattg aatacgtcag    2640
aatgttatca caacacccat atattaaacc tgcttatttg gctggtaaag ttctgttgg     2700 taaagcttac tcagaagttg tcagatggca aacagttggt caagtcccaa aggaagtagc    2760
cgatatgcca gttttgccta ccgacgtcaa tgaaatcaaa aaggctggtg tagatattgt    2820
tttctctcca ttacctcaag gtgctgcagg tccagttgaa gaagaatttg caaaagccgg    2880
tttccctgtc atttctaatt caccagatca tagattcgat ccagacgtac ctttgatgat    2940
acctgaagtt aacggtcaca ctgcatcctt aattgatgaa caaagaaaa gaagagactg     3000 gagtggtttt attgttacta caccattgtg tacagcacaa ggtattgcca taccattagc    3060
tcctatctat agagatttca gagttgattc tgtattcata accactatgc aatccttgag    3120
tggtgaaggt tatcctggtg ttgcttcatt ggatgtagtt gacaacatca aggttttggg    3180
tgacgcttac gacgctaaaa ctgttaagga agtcacaaga atttatctg aagttaagag     3240 aaacgtccca ggtactatgg atgaattgac tttatcagca acaacccata gaatagccac    3300
cattcatggt cactacgaag taatgtacgt tacttttaaa gaagatgtca aggtagaaaa    3360
ggttaaggaa actttggcta acttcaaagg tgaacctcaa gatatgaagt taccaacagc    3420
accttccaga ccaatcttga ttaccgaatt agataacaga ccacaacctt acttcgatag    3480
atgggcaggt gacgttccag gtatgtccgt cgtagttggt agattaaagc aagttaacaa    3540
cagaactgtt agattggttt ctttgatcca taacacagtc agaggtgccg ctggtggtgg    3600 tatttttggta gccgaatatt tgatcgaaaa gggttacatc cctaagtgaa tcgatggaga    3660
```

```
ttgataagac ttttctagtt gcatatcttt tatatttaaa tcttatctat tagttaattt    3720
tttgtaattt atccttatat atagtctggt tattctaaaa tatcatttca gtatctaaaa    3780
attcccctct tttttcagtt atatcttaac aggcgacagt ccaaatgttg atttatccca    3840
gtccgattca tcagggttgt gaagcatttt gtcaatggtc gaaatcacat cagtaatagt    3900
gcctcttact tgcctcatag aatttctttc tcttaacgtc accgtttggt cttttatagt    3960
ttcgaaatct atggtgatac caaatggtgt tcccaattca tcgttacggg cgtatttttt    4020
accaattgaa gtattggaat cgtcaatttt aaagtgaatt cgaataaaaa acacgctttt    4080
tcagttcgag tttatcatta tcaatactgc catttcaaag aatacgtaaa taattaatag    4140
tagtgatttt cctaaccttta tttagtcaaa aaattagcct tttaattctg ctgtaacccg    4200
tacatgccca aaataggggg cgggttacac agaatatata acatcgtagg tgtctgggtg    4260
aacagtttat tcctggcatc cactaaatat aatggagccc gcttttaag ctggcatcca     4320 gaaaaaaaaa gaatcccagc accaaaatat tgttttcttc accaaccatc agttcatagg    4380
tccattctct tagcgcaact acagagaaca ggggcacaaa caggcaaaaa acgggcacaa    4440
cctcaatgga gtgatgcaac ctgcctggag taaatgatga cacaaggcaa ttgacccacg    4500
catgtatcta tctcatttc ttacaccttc tattaccttc tgctctctct gatttggaaa     4560
aagctgaaaa aaaaggttga aaccagttcc ctgaaattat tcccctactt gactaataag    4620
tatataaaga cggtaggtat tgattgtaat tctgtaaatc tatttcttaa acttcttaaa    4680
ttctactttt atagttagtc tttttttag ttttaaaaca ccaagaactt agtttcgaat     4740
aaacacacat aaacaaacaa acccgggaac aaaatggtca acttacaagg taaaacagca    4800
ttggtcactg gttcaacatc aggtatcggt ttgggtatcg cagaagcatt gggtagagcc    4860
ggtgctaata tagtattaaa cggttttggt gacgttgatg ctgcattggc aacaatcgcc    4920
gctaccggtg cacaatctgc ccatcaccca gctgatatga gaaaacctga cgaaattgaa    4980
gcaatgatag ctatggcaag agaaagattc ggtaccgttg atgtcttagt aaataacgct    5040
ggtattcaac atgttgcaca agtcgaagat tttccagcac aaaagtggga tgacatcttg    5100
gccataaatt tgacttcttc attccatact acaagacacg ttatacctgc tatgagagca    5160
agaaattggg gtagaatcgt taacattgct tcagtacatg gtttagttgg ttccgccggt    5220
aaaagtgctt atgttgcagc caagcacggt ttagtcggtt tgaccaaagt aactgcattg    5280
gaaacagccg gtaccggtat cacttgtaat gctatttgcc caggttttgt tttaacacct    5340
ttggtcgctg cacaaatagc tgctattgct aaaagagatg gtatttctat ggaagccgct    5400
agagctagat tgttatctga taagcaacca tcaggtcaat ttgtcactcc tgaacaattg    5460
ggtaacttgg tttaatgtt gtgtagtcca ttcggtgacc aagttagagg tgcagcctgg    5520
gctatggatg gtggttggac agctcaatga ggatccgtga atttacttta aatcttgcat    5580
ttaaataaat tttcttttta tagctttatg acttagtttc aatttatata ctattttaat    5640
gacattttcg attcattgat tgaaagcttt gtgttttttc ttgatgcgct attgcattgt    5700 tcttgtctttt ttcgccacat gtaatatctg tagtagatac ctgatacatt gtggatgctg    5760
agtgaaattt tagttaataa tggaggcgct cttaataatt ttggggatat tggcttttttt  5820 ttttaaagtt tacaaatgaa ttttttccgc caggatacta gtcatgcgac tgggtgagca    5880
tatgttccgc tgatgtgatg tgcaagataa acaagcaagg cagaaactaa cttcttcttc    5940
atgtaataaa cacaccccgc gtttatttac ctatctctaa acttcaacac cttatatcat    6000
aactaatatt tcttgagata agcacactgc acccatacct tccttaaaaa cgtagcttcc    6060
```

```
agtttttggt ggttccggct tccttcccga ttccgcccgc taaacgcata ttttgttgc      6120
ctggtggcat ttgcaaaatg cataacctat gcatttaaaa gattatgtat gctcttctga      6180
cttttcgtgt gatgaggctc gtggaaaaaa tgaataattt atgaatttga gaacaatttt      6240
gtgttgttac ggtattttac tatggaataa tcaatcaatt gaggatttta tgcaaatatc      6300
gtttgaatat ttttccgacc ctttgagtac ttttcttcat aattgcataa tattgtccgc      6360
tgccccttt tctgttagac ggtgtcttga tctacttgct atcgttcaac accaccttat       6420
tttctaacta ttttttttt agctcatttg aatcagctta tggtgatggc acattttgc        6480
ataaacctag ctgtcctcgt tgaacatagg aaaaaaaat atataaacaa ggctctttca       6540
ctctccttgc aatcagattt gggtttgttc cctttatttt catatttctt gtcatattcc      6600
tttctcaatt attattttct actcataacc tcacgcaaaa taacacagtc aaatcaatca      6660
aagcggccgc aacaaaatgg aacactccgt cattgaacca accgtccctac tgcctttgcc     6720
agctatgttt gatgccccct caggtatctt ctcctcctta gacgatgcag ttcaagccgc      6780
tactttagcc caacaacaat tgtcatccgt tgaattgaga caacaagtca taaaggcaat     6840
tagagttgcc ggtgaaagat acgctcaagt cttggcagaa atggccgtcg cagaaaccgg      6900
tatgggtaga gttgtagata atacattaa gaatgtttca caagcaagac atacaccagg     6960
tatcgaatgt ttatccgctg aagtattaac aggtgacaac ggtttgacct tgattgaaaa     7020
tgcaccttgg ggtgttgttg cttccgttac accatcaacc aacccagctg ctacagttat     7080
taacaacgca atttctatga tcgctgccgg taactcagtt gtctttgcac ctcatccatc     7140
tgcaaagaat gtttccttaa gaactatctc cttgttgaat aaggcaatag tagccacagg     7200
tggtccagaa aatttgttag tctctgttgc aaaccctaat atcgaaactg cacaaagatt     7260
gtttagatat ccaggtatcg gtttgttggt tgtaaccggt ggtgaagctg tagtcgaagc     7320
tgcaagaaag cataccgata aaagattaat cgctgcaggt gcaggtaatc caccagttgt     7380
tgttgacgaa acagctgata tccctaaggc agcaagagcc attgttaaag gtgcatcatt     7440
cgataacaat attatctgtg ccgatgaaaa gtttaattg gtagttgaca gagttgccga     7500
tgcattattg gccgaaatgc aaagaaataa cgcagtatta ttgactccag aacaaacaga     7560
aagattgtta ccagctttgt tatctgatat cgacgaacaa ggtaaaggta gagttaacag     7620
agactacgtt ggtagagatg ccgctaaatt agcagctgca atcggtttgg aagtctcaga     7680
acatacaaga ttattgttgg cagaaacaga tgcagatcat ccattcgctg ttacagaatt     7740
aatgatgcca gttttacctg tcatcagagt caagaacgtt gatgacgcaa ttgctttggc     7800
agtcaaattg gaatctggtt gtagacatac tgctgctatg cattcaacca acataagaaa     7860
tttgaataga atggccaacg ctataaatac atcaatattc gttaagaatg gtccttgtat     7920
cgctggttta ggtttgggtg gtgaaggttg acaagtatg acaatcagta ccccaactgg      7980
tgaaggtgtt acatcagcta gaacctttgt tagattgaga agatgcgtct tagtagatat     8040
gtttagaata gcctaaccgc gggcgattta atctctaatt attagttaaa gttttataag     8100
catttttatg taacgaaaaa taaattggtt catattatta ctgcactgtc acttaccatg     8160
gaaagaccag acaagaagtt gccgacagtc tgttgaattg gcctggttag gcttaagtct     8220
gggtccgctt ctttacaaat ttggagaatt tctcttaaac gatatgtata ttcttttcgt     8280
tggaaaagat ttcttccaaa aaaaaaccg atgaattagt ggaaccaagg aaaaaaaag      8340
aggtatcctt gattaaggaa cactgtttaa acagtgtggt ttccaaaacc ctgaaactgc     8400
```

-continued

```
attagtgtaa tacaagacta gacacctcga tacaaataat ggttactcaa ttcaaaactg      8460
ccgagctcta gtacctcggc gatcgctgct ggtataccta taaatattta tgtactttct      8520
ataccagtac tttactaata atatatatat gtatatctta ttttatttaa aattctttaa      8580
tcgattttat tatgcgttga cgacgaaaat gtaaacaaag cgcgaaaacg cgataatgaa      8640
aatatgagat cgatcctaaa ttaatggact agttatatca acactgacac atggaggaca      8700
taataactta gaaaagtttc aactttgtaa gtagcaaaga atagccagga attttttcaga     8760 caaatatgaa tagactgcgt agtcaacaaa gtacaaagag accatgtgct gtttgtacga      8820
aacgtaaagt taaatgtgat agaaagatac cttgtggaaa ctgtattaaa agaggccaag      8880
aagctgaatg tatcaaaacg gtgacaaatg gttttttaca tgacccacat tctacaaacg      8940
gaacagattc aattcttaat atccttcgaa tgtggccaag ttatgaatat tggataactg      9000
atattggttt attcaagaca aaagatatag attcaactat cagaatcgaa actctagaag      9060
atgaactaag agagatcact ttttggaccg attatttaac aatggaatct tcctttaagc      9120
tattaaattt tgcagtggag aacctaggcc ccttatattt tggttgtcta ggtgatatca      9180
gtgaattatt tgtacagcta gagaattact ggactagaag aaatcaattc aaagaaaatc      9240
caagggaaac cacgttcact ttagacgata attactggaa ttcagtacta tgggcaattt      9300
tcacaatggc catctactat ataccgttag aaaatttatc tgatgaattc gaattacagt      9360
ctatctgtga acaattaaat atagatgaga atcaacattg gtctgaatca attcaattga      9420
cagttgtgca aggttttaca aaatgttgta tggatcattt gaacagagca aaatataacg      9480
agaatccggc gcgcccagct tttgttccct ttagtgaggg ttaatttcga gcttggcgta      9540
atcatggtca tagctgtttc ctgtgtgaaa ttgttatccg ctcacaattc cacacaacat      9600
acgagccgga agcataaagt gtaaagcctg gggtgcctaa tgagtgagct aactcacatt      9660
aattgcgttg cgctcactgc ccgctttcca gtcgggaaac ctgtcgtgcc agctgcatta      9720
atgaatcggc caacgcgcgg ggagaggcgg tttgcgtatt gggcgctctt ccgcttcctc      9780
gctcactgac tcgctgcgct cggtcgttcg gctgcggcga gcggtatcag ctcactcaaa      9840
ggcggtaata cggttatcca cagaatcagg ggataacgca ggaaagaaca tgtgagcaaa      9900
aggccagcaa aaggccagga accgtaaaaa ggccgcgttg ctggcgtttt tccataggct      9960
ccgcccccct gacgagcatc acaaaaatcg acgctcaagt cagaggtggc gaaacccgac     10020
aggactataa agataccagg cgtttccccc tggaagctcc ctcgtgcgct ctcctgttcc     10080
gaccctgccg cttaccggat acctgtccgc ctttctccct tcgggaagcg tggcgctttc     10140
tcatagctca cgctgtaggt atctcagttc ggtgtaggtc gttcgctcca agctgggctg     10200
tgtgcacgaa ccccccgttc agcccgaccg ctgcgcctta tccggtaact atcgtcttga     10260
gtccaacccg gtaagacacg acttatcgcc actggcagca gccactggta acaggattag     10320
cagagcgagg tatgtaggcg gtgctacaga gttcttgaag tggtggccta actacggcta     10380
cactagaagg acagtatttg gtatctgcgc tctgctgaag ccagttacct tcggaaaaag     10440
agttggtagc tcttgatccg gcaaacaaac caccgctggt agcggtggtt ttttgtttg      10500 caagcagcag attacgcgca gaaaaaaagg atctcaagaa gatcctttga tcttttctac     10560
ggggtctgac gctcagtgga acgaaaactc acgttaaggg attttggtca tgagattatc     10620
aaaaaggatc ttcacctaga tccttttaaa ttaaaaatga agttttaaat caatctaaag     10680
tatatatgag taaacttggt ctgacagtta ccaatgctta atcagtgagg cacctatctc     10740
agcgatctgt ctatttcgtt catccatagt tgcctgactc cccgtcgtgt agataactac     10800
```

```
gatacgggag ggcttaccat ctggccccag tgctgcaatg ataccgcgag acccacgctc   10860
accggctcca gatttatcag caataaacca gccagccgga agggccgagc gcagaagtgg   10920
tcctgcaact ttatccgcct ccatccagtc tattaattgt tgccgggaag ctagagtaag   10980
tagttcgcca gttaatagtt tgcgcaacgt tgttgccatt gctacaggca tcgtggtgtc   11040
acgctcgtcg tttggtatgg cttcattcag ctccggttcc caacgatcaa ggcgagttac   11100
atgatccccc atgttgtgca aaaaagcggt tagctccttc ggtcctccga tcgttgtcag   11160
aagtaagttg gccgcagtgt tatcactcat ggttatggca gcactgcata attctcttac   11220
tgtcatgcca tccgtaagat gcttttctgt gactggtgag tactcaacca agtcattctg   11280
agaatagtgt atgcggcgac cgagttgctc ttgcccggcg tcaatacggg ataataccgc   11340
gccacatagc agaactttaa aagtgctcat cattggaaaa cgttcttcgg ggcgaaaact   11400
ctcaaggatc ttaccgctgt tgagatccag ttcgatgtaa cccactcgtg cacccaactg   11460
atcttcagca tcttttactt tcaccagcgt ttctgggtga gcaaaaacag gaaggcaaaa   11520
tgccgcaaaa aagggaataa gggcgacacg gaaatgttga atactcatac tcttcctttt   11580
tcaatattat tgaagcattt atcagggtta ttgtctcatg agcggataca tatttgaatg   11640
tatttagaaa aataaacaaa tagggttcc gcgcacattt ccccgaaaag tgc           11693

<210> SEQ ID NO 9
<211> LENGTH: 61
<212> TYPE: DNA
<213> ORGANISM: Artificial Sequence
<220> FEATURE:
<223> OTHER INFORMATION: primer

<400> SEQUENCE: 9
cttcaaagtt cttctcattt tgttgtcgac ttttgtttat aatttatcaa atatgttgat   60
t                                                                   61

<210> SEQ ID NO 10
<211> LENGTH: 23
<212> TYPE: DNA
<213> ORGANISM: Artificial Sequence
<220> FEATURE:
<223> OTHER INFORMATION: oligomer for Gibson assembly

<400> SEQUENCE: 10
gtcgacaaca aaatgagaag aac                                           23

<210> SEQ ID NO 11
<211> LENGTH: 62
<212> TYPE: DNA
<213> ORGANISM: Artificial Sequence
<220> FEATURE:
<223> OTHER INFORMATION: oligomer for Gibson assembly

<400> SEQUENCE: 11
ctttcaagac tcttctcatt tgttgtcga cttttgttta taatttatca aatatgttga   60
tt                                                                  62

<210> SEQ ID NO 12
<211> LENGTH: 24
<212> TYPE: DNA
<213> ORGANISM: Artificial Sequence
<220> FEATURE:
<223> OTHER INFORMATION: oligomer for Gibson assembly
```

```
<400> SEQUENCE: 12
gtcgacaaca aaatgagaag agtc                                          24

<210> SEQ ID NO 13
<211> LENGTH: 57
<212> TYPE: DNA
<213> ORGANISM: Artificial Sequence
<220> FEATURE:
<223> OTHER INFORMATION: oligomer for Gibson assembly

<400> SEQUENCE: 13
tacgactcac tatagggcga attgcctgca gggttaactc agttttctct ctttccc      57

<210> SEQ ID NO 14
<211> LENGTH: 59
<212> TYPE: DNA
<213> ORGANISM: Artificial Sequence
<220> FEATURE:
<223> OTHER INFORMATION: oligomer for Gibson assembly

<400> SEQUENCE: 14
actagagctc cctcggacgt gggccctttt aaatgatttt tatttgtatt gatatatgg    59

<210> SEQ ID NO 15
<211> LENGTH: 70
<212> TYPE: DNA
<213> ORGANISM: Artificial Sequence
<220> FEATURE:
<223> OTHER INFORMATION: oligomer for Gibson assembly

<400> SEQUENCE: 15
gggcccacgt ccgagggagc tctagtacct cggcgatcgc tttgtcttta tttttgaaat  60
gttaatagtc                                                          70

<210> SEQ ID NO 16
<211> LENGTH: 56
<212> TYPE: DNA
<213> ORGANISM: Artificial Sequence
<220> FEATURE:
<223> OTHER INFORMATION: oligomer for Gibson assembly

<400> SEQUENCE: 16
taaccctcac taaagggaac aaaagctggg cgcgcccttt tgcagttgcg gatttc       56

<210> SEQ ID NO 17
<211> LENGTH: 44
<212> TYPE: DNA
<213> ORGANISM: Artificial Sequence
<220> FEATURE:
<223> OTHER INFORMATION: oligomer for Gibson assembly

<400> SEQUENCE: 17
ggttacatcc ctaagtgaat cgatggagat tgataagact tttc                    44

<210> SEQ ID NO 18
<211> LENGTH: 40
<212> TYPE: DNA
<213> ORGANISM: Artificial Sequence
<220> FEATURE:
<223> OTHER INFORMATION: oligomer for Gibson assembly

<400> SEQUENCE: 18
caaaagtcga acaaaaatg agaagaactt tgaaggctgc                          40
```

```
<210> SEQ ID NO 19
<211> LENGTH: 59
<212> TYPE: DNA
<213> ORGANISM: Artificial Sequence
<220> FEATURE:
<223> OTHER INFORMATION: oligomer for Gibson assembly

<400> SEQUENCE: 19
cttcaaagtt cttctcattt tgttgtcgac ttttgtttat aatttattga aatatgttg      59

<210> SEQ ID NO 20
<211> LENGTH: 89
<212> TYPE: DNA
<213> ORGANISM: Artificial Sequence
<220> FEATURE:
<223> OTHER INFORMATION: oligomer for Gibson assembly

<400> SEQUENCE: 20
ctgtagcacc taaaatggca gccttcaaag ttcttctcat ttttaaatga tttttatttg     60
tattgatata tggatatata tgtgtacgg                                       89

<210> SEQ ID NO 21
<211> LENGTH: 89
<212> TYPE: DNA
<213> ORGANISM: Artificial Sequence
<220> FEATURE:
<223> OTHER INFORMATION: oligomer for Gibson assembly

<400> SEQUENCE: 21
ggttacatcc ctaagtgagt catttaattt attcttttag aatataatta ttttgtcttt     60
atttttgaaa tgttaatagt ctttttttt                                       89

<210> SEQ ID NO 22
<211> LENGTH: 81
<212> TYPE: DNA
<213> ORGANISM: Artificial Sequence
<220> FEATURE:
<223> OTHER INFORMATION: oligomer for Gibson assembly

<400> SEQUENCE: 22
ccgtacacat atatatccat atatcaatac aaataaaaat catttaaaaa tgagaagaac     60
tttgaaggct gccatttag g                                                81

<210> SEQ ID NO 23
<211> LENGTH: 89
<212> TYPE: DNA
<213> ORGANISM: Artificial Sequence
<220> FEATURE:
<223> OTHER INFORMATION: oligomer for Gibson assembly

<400> SEQUENCE: 23
atttcaaaaa taaagacaaa ataattatat tctaaaagaa taaattaaat gactcactta     60
gggatgtaac ccttttcgat caaatattc                                       89

<210> SEQ ID NO 24
<211> LENGTH: 43
<212> TYPE: DNA
<213> ORGANISM: Artificial Sequence
<220> FEATURE:
<223> OTHER INFORMATION: oligomer for Gibson assembly

<400> SEQUENCE: 24
aaattcgggc ccgttaactc agtttttctct ctttccctcc acc                      43
```

```
<210> SEQ ID NO 25
<211> LENGTH: 61
<212> TYPE: DNA
<213> ORGANISM: Artificial Sequence
<220> FEATURE:
<223> OTHER INFORMATION: oligomer for Gibson assembly

<400> SEQUENCE: 25
tttgttgtcg acttttaaat gatttttatt tgtattgata tatggatata tatgtgtacg    60
g                                                                    61

<210> SEQ ID NO 26
<211> LENGTH: 30
<212> TYPE: DNA
<213> ORGANISM: Artificial Sequence
<220> FEATURE:
<223> OTHER INFORMATION: oligomer for Gibson assembly

<400> SEQUENCE: 26
tgctacctta atttctcatg gaaagtggca                                     30

<210> SEQ ID NO 27
<211> LENGTH: 34
<212> TYPE: DNA
<213> ORGANISM: Artificial Sequence
<220> FEATURE:
<223> OTHER INFORMATION: oligomer for Gibson assembly

<400> SEQUENCE: 27
gttaacgagt ttaatgttta aaagcgtata taag                                34

<210> SEQ ID NO 28
<211> LENGTH: 87
<212> TYPE: DNA
<213> ORGANISM: Artificial Sequence
<220> FEATURE:
<223> OTHER INFORMATION: oligomer for Gibson assembly

<400> SEQUENCE: 28
aatctcaccg tacacatata tatccatata tcaatacaaa taaaaatcat ttaaaaatga    60
gaagagtctt gaaagcagca atcttgg                                        87

<210> SEQ ID NO 29
<211> LENGTH: 87
<212> TYPE: DNA
<213> ORGANISM: Artificial Sequence
<220> FEATURE:
<223> OTHER INFORMATION: oligomer for Gibson assembly

<400> SEQUENCE: 29
gtggaaccca agattgctgc tttcaagact cttctcattt ttaaatgatt tttatttgta    60
ttgatatatg gatatatatg tgtacgg                                        87

<210> SEQ ID NO 30
<211> LENGTH: 87
<212> TYPE: DNA
<213> ORGANISM: Artificial Sequence
<220> FEATURE:
<223> OTHER INFORMATION: oligomer for Gibson assembly

<400> SEQUENCE: 30
tggtattttg gcaacagaat ttttggttga aaagggttac atggattgat tgtctttat    60 ttttgaaatg ttaatagtct ttttttt                                        87
```

<210> SEQ ID NO 31
<211> LENGTH: 87
<212> TYPE: DNA
<213> ORGANISM: Artificial Sequence
<220> FEATURE:
<223> OTHER INFORMATION: oligomer for Gibson assembly

<400> SEQUENCE: 31
tttgttcaaa gtaaaaaaaa aagactatta acatttcaaa aataaagaca aatcaatcca    60 tgtaacccctt ttcaaccaaa aattctg    87

<210> SEQ ID NO 32
<211> LENGTH: 22
<212> TYPE: DNA
<213> ORGANISM: Artificial Sequence
<220> FEATURE:
<223> OTHER INFORMATION: primer for qPCR

<400> SEQUENCE: 32
cggactttag agccttgtag ac    22

<210> SEQ ID NO 33
<211> LENGTH: 21
<212> TYPE: DNA
<213> ORGANISM: Artificial Sequence
<220> FEATURE:
<223> OTHER INFORMATION: primer for qPCR

<400> SEQUENCE: 33
atctggttac actcacgatg g    21

<210> SEQ ID NO 34
<211> LENGTH: 22
<212> TYPE: DNA
<213> ORGANISM: Artificial Sequence
<220> FEATURE:
<223> OTHER INFORMATION: primer for qPCR

<400> SEQUENCE: 34
ccaagtacgt tagagctaac gg    22

<210> SEQ ID NO 35
<211> LENGTH: 20
<212> TYPE: DNA
<213> ORGANISM: Artificial Sequence
<220> FEATURE:
<223> OTHER INFORMATION: primer for qPCR

<400> SEQUENCE: 35
gagcttctct ggtatcagct    20

<210> SEQ ID NO 36
<211> LENGTH: 22
<212> TYPE: DNA
<213> ORGANISM: Artificial Sequence
<220> FEATURE:
<223> OTHER INFORMATION: primer for qPCR

<400> SEQUENCE: 36
agctttagca aacattagac cc    22

<210> SEQ ID NO 37
<211> LENGTH: 21
<212> TYPE: DNA

```
<213> ORGANISM: Artificial Sequence
<220> FEATURE:
<223> OTHER INFORMATION: primer for qPCR

<400> SEQUENCE: 37
attccatccg aatatgctgg t                                             21

<210> SEQ ID NO 38
<211> LENGTH: 22
<212> TYPE: DNA
<213> ORGANISM: Artificial Sequence
<220> FEATURE:
<223> OTHER INFORMATION: primer for qPCR

<400> SEQUENCE: 38
ggaacctaaa tgactgttgg ca                                            22

<210> SEQ ID NO 39
<211> LENGTH: 21
<212> TYPE: DNA
<213> ORGANISM: Artificial Sequence
<220> FEATURE:
<223> OTHER INFORMATION: primer for qPCR

<400> SEQUENCE: 39
aggatgttga tttcgactcg t                                             21

<210> SEQ ID NO 40
<211> LENGTH: 24
<212> TYPE: DNA
<213> ORGANISM: Artificial Sequence
<220> FEATURE:
<223> OTHER INFORMATION: primer for qPCR

<400> SEQUENCE: 40
ttccaaaggg taccaattta gctg                                          24

<210> SEQ ID NO 41
<211> LENGTH: 23
<212> TYPE: DNA
<213> ORGANISM: Artificial Sequence
<220> FEATURE:
<223> OTHER INFORMATION: primer for qPCR

<400> SEQUENCE: 41
gtaccgctaa tgaacctaaa cca                                           23

<210> SEQ ID NO 42
<211> LENGTH: 21
<212> TYPE: DNA
<213> ORGANISM: Artificial Sequence
<220> FEATURE:
<223> OTHER INFORMATION: primer for qPCR

<400> SEQUENCE: 42
agagctgaca ctagagaagc c                                             21

<210> SEQ ID NO 43
<211> LENGTH: 23
<212> TYPE: DNA
<213> ORGANISM: Artificial Sequence
<220> FEATURE:
<223> OTHER INFORMATION: primer for qPCR

<400> SEQUENCE: 43
gatgtgtcta cgacgtatct acc                                           23
```

<210> SEQ ID NO 44
<211> LENGTH: 20
<212> TYPE: DNA
<213> ORGANISM: Artificial Sequence
<220> FEATURE:
<223> OTHER INFORMATION: primer for qPCR

<400> SEQUENCE: 44
gtactggtaa cgtccaagtc                                          20

<210> SEQ ID NO 45
<211> LENGTH: 21
<212> TYPE: DNA
<213> ORGANISM: Artificial Sequence
<220> FEATURE:
<223> OTHER INFORMATION: primer for qPCR

<400> SEQUENCE: 45
gaacccttcc atactctacc a                                        21

<210> SEQ ID NO 46
<211> LENGTH: 21
<212> TYPE: DNA
<213> ORGANISM: Artificial Sequence
<220> FEATURE:
<223> OTHER INFORMATION: primer for qPCR

<400> SEQUENCE: 46
ttcagttcgt gctactcaag g                                        21

<210> SEQ ID NO 47
<211> LENGTH: 20
<212> TYPE: DNA
<213> ORGANISM: Artificial Sequence
<220> FEATURE:
<223> OTHER INFORMATION: primer for qPCR

<400> SEQUENCE: 47
tcaattgcaa cgacagagac                                          20

<210> SEQ ID NO 48
<211> LENGTH: 22
<212> TYPE: DNA
<213> ORGANISM: Artificial Sequence
<220> FEATURE:
<223> OTHER INFORMATION: primer for qPCR

<400> SEQUENCE: 48
ccgtaccctg aagagtttac tg                                       22

<210> SEQ ID NO 49
<211> LENGTH: 24
<212> TYPE: DNA
<213> ORGANISM: Artificial Sequence
<220> FEATURE:
<223> OTHER INFORMATION: primer for qPCR

<400> SEQUENCE: 49
caaccataga ttcacgaatt gctc                                     24

<210> SEQ ID NO 50
<211> LENGTH: 22
<212> TYPE: DNA
<213> ORGANISM: Artificial Sequence
<220> FEATURE:

<223> OTHER INFORMATION: primer for qPCR

<400> SEQUENCE: 50
agtggatttg gattaatggg tg                                    22

<210> SEQ ID NO 51
<211> LENGTH: 22
<212> TYPE: DNA
<213> ORGANISM: Artificial Sequence
<220> FEATURE:
<223> OTHER INFORMATION: primer for qPCR

<400> SEQUENCE: 51
gcttctgtaa cacctttaac ac                                    22

<210> SEQ ID NO 52
<211> LENGTH: 20
<212> TYPE: DNA
<213> ORGANISM: Artificial Sequence
<220> FEATURE:
<223> OTHER INFORMATION: primer for qPCR

<400> SEQUENCE: 52
aaattggtga ccgtgttggt                                       20

<210> SEQ ID NO 53
<211> LENGTH: 23
<212> TYPE: DNA
<213> ORGANISM: Artificial Sequence
<220> FEATURE:
<223> OTHER INFORMATION: primer for qPCR

<400> SEQUENCE: 53
aaccaccttt actacggtaa cca                                   23

<210> SEQ ID NO 54
<211> LENGTH: 22
<212> TYPE: DNA
<213> ORGANISM: Artificial Sequence
<220> FEATURE:
<223> OTHER INFORMATION: primer for qPCR

<400> SEQUENCE: 54
tttagtcgtc atctgttcag gt                                    22

<210> SEQ ID NO 55
<211> LENGTH: 23
<212> TYPE: DNA
<213> ORGANISM: Artificial Sequence
<220> FEATURE:
<223> OTHER INFORMATION: primer for qPCR

<400> SEQUENCE: 55
gagacaccta acaaaccaaa tgg                                   23

<210> SEQ ID NO 56
<211> LENGTH: 24
<212> TYPE: DNA
<213> ORGANISM: Artificial Sequence
<220> FEATURE:
<223> OTHER INFORMATION: primer for qPCR

<400> SEQUENCE: 56
gattcaagct tcttctcgta tcgg                                  24

<210> SEQ ID NO 57
<211> LENGTH: 23
<212> TYPE: DNA
<213> ORGANISM: Artificial Sequence
<220> FEATURE:
<223> OTHER INFORMATION: primer for qPCR

<400> SEQUENCE: 57
ggaaatgata ccattcacga cct                                          23

<210> SEQ ID NO 58
<211> LENGTH: 22
<212> TYPE: DNA
<213> ORGANISM: Artificial Sequence
<220> FEATURE:
<223> OTHER INFORMATION: primer for qPCR

<400> SEQUENCE: 58
gttccgtcaa agaaatcaag ca                                           22

<210> SEQ ID NO 59
<211> LENGTH: 24
<212> TYPE: DNA
<213> ORGANISM: Artificial Sequence
<220> FEATURE:
<223> OTHER INFORMATION: primer for qPCR

<400> SEQUENCE: 59
tggtaaacct gtatctgaca tcac                                         24

<210> SEQ ID NO 60
<211> LENGTH: 22
<212> TYPE: DNA
<213> ORGANISM: Artificial Sequence
<220> FEATURE:
<223> OTHER INFORMATION: primer for qPCR

<400> SEQUENCE: 60
tttagttgtc atttgtgccg gt                                           22

<210> SEQ ID NO 61
<211> LENGTH: 22
<212> TYPE: DNA
<213> ORGANISM: Artificial Sequence
<220> FEATURE:
<223> OTHER INFORMATION: primer for qPCR

<400> SEQUENCE: 61
gacacctaac aaaccaaacg ga                                           22

<210> SEQ ID NO 62
<211> LENGTH: 22
<212> TYPE: DNA
<213> ORGANISM: Artificial Sequence
<220> FEATURE:
<223> OTHER INFORMATION: primer for qPCR

<400> SEQUENCE: 62
gctaacttca aaggtgaacc tc                                           22

<210> SEQ ID NO 63
<211> LENGTH: 21
<212> TYPE: DNA
<213> ORGANISM: Artificial Sequence
<220> FEATURE:
<223> OTHER INFORMATION: primer for qPCR

<400> SEQUENCE: 63
aatctaccaa ctacgacgga c					21

<210> SEQ ID NO 64
<211> LENGTH: 22
<212> TYPE: DNA
<213> ORGANISM: Artificial Sequence
<220> FEATURE:
<223> OTHER INFORMATION: primer for qPCR

<400> SEQUENCE: 64
cagattcgaa ccagatatcc ct				22

<210> SEQ ID NO 65
<211> LENGTH: 24
<212> TYPE: DNA
<213> ORGANISM: Artificial Sequence
<220> FEATURE:
<223> OTHER INFORMATION: primer for qPCR

<400> SEQUENCE: 65
ccaatggtaa caatacacct tgag				24

<210> SEQ ID NO 66
<211> LENGTH: 24
<212> TYPE: DNA
<213> ORGANISM: Artificial Sequence
<220> FEATURE:
<223> OTHER INFORMATION: primer for qPCR

<400> SEQUENCE: 66
ggtaaagctt actcagaagt tgtc				24

<210> SEQ ID NO 67
<211> LENGTH: 20
<212> TYPE: DNA
<213> ORGANISM: Artificial Sequence
<220> FEATURE:
<223> OTHER INFORMATION: primer for qPCR

<400> SEQUENCE: 67
cagcaccttg aggtaatgga					20

<210> SEQ ID NO 68
<211> LENGTH: 20
<212> TYPE: DNA
<213> ORGANISM: Artificial Sequence
<220> FEATURE:
<223> OTHER INFORMATION: primer for qPCR

<400> SEQUENCE: 68
ctatgcaagc tgtttccggt					20

<210> SEQ ID NO 69
<211> LENGTH: 24
<212> TYPE: DNA
<213> ORGANISM: Artificial Sequence
<220> FEATURE:
<223> OTHER INFORMATION: primer for qPCR

<400> SEQUENCE: 69
cgttgacgtt tctcttagtt tcag				24

<210> SEQ ID NO 70
<211> LENGTH: 20

```
<212> TYPE: DNA
<213> ORGANISM: Artificial Sequence
<220> FEATURE:
<223> OTHER INFORMATION: primer for qPCR

<400> SEQUENCE: 70
ctttgagtgc aagtatcgcc                                                   20

<210> SEQ ID NO 71
<211> LENGTH: 22
<212> TYPE: DNA
<213> ORGANISM: Artificial Sequence
<220> FEATURE:
<223> OTHER INFORMATION: primer for qPCR

<400> SEQUENCE: 71
tgtgtaattg ttcaccaaag cc                                                22

<210> SEQ ID NO 72
<211> LENGTH: 21
<212> TYPE: DNA
<213> ORGANISM: Artificial Sequence
<220> FEATURE:
<223> OTHER INFORMATION: primer for qPCR

<400> SEQUENCE: 72
gagatagcac accattcacc a                                                 21

<210> SEQ ID NO 73
<211> LENGTH: 24
<212> TYPE: DNA
<213> ORGANISM: Artificial Sequence
<220> FEATURE:
<223> OTHER INFORMATION: primer

<400> SEQUENCE: 73
caacgttaag tactctggtg tttg                                              24

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
atgagaagaa ctttgaaggc tg                                                22

<210> SEQ ID NO 75
<211> LENGTH: 26
<212> TYPE: DNA
<213> ORGANISM: Artificial Sequence
<220> FEATURE:
<223> OTHER INFORMATION: primer

<400> SEQUENCE: 75
ttacttaggg atgtaaccct tttcga                                            26

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
```

```
atgaaaattt ttgcttatgg                                          20

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
ttaatattca acagcaatag                                          20

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
atggttttgc attctaaagt                                          20

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
ttaacaagaa gatttagaaa                                          20

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
atgtcttcta tgccaaatca                                          20

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
ttatttattt tccaattcag                                          20
```

PROMOTER DERIVED FROM ORGANIC ACID-RESISTANT YEAST AND METHOD FOR EXPRESSION OF TARGET GENE BY USING SAME

CROSS REFERENCE TO RELATED APPLICATIONS

This application is a national phase of PCT application No. PCT/KR2019/002432, filed Feb. 28, 2019, which claims priority to KR patent application No. 1020180044508 filed Apr. 17, 2018, all of which are incorporated herein by reference thereto.

SEQUENCE LISTING

The instant application contains a Sequence Listing which has been submitted in ASCII format via EFS-Web and is hereby incorporated by reference in its entirety. Said ASCII copy, created on Oct. 15, 2020, is named 216870_PFB2478_ST25_Seq.txt and is 61,228 bytes in size.

TECHNICAL FIELD

The present invention relates to a novel promoter derived from an organic acid-resistant yeast, and more particularly, to a novel promoter for regulating ADH gene expression in an organic acid-resistant yeast, and a method of producing an organic acid by expressing an organic acid production-related gene using the same.

BACKGROUND ART

Bioconversion of various raw materials into chemicals, such as organic acids, alcohols and amines, through bioprocesses, has attracted attention in terms of environmental friendliness, carbon dioxide reduction, sustainability, and supply of new platform chemicals. Through this bioconversion, foods, cosmetics, nutraceuticals and drug-related chemical products have been provided.

However, in general, products that are produced through bioconversion need to undergo a purification process of removing impurities. In the production of organic acids, fermentation is often performed at a neutral pH adjusted by a base in order to prevent the growth of strains from being inhibited by the produced organic acids, and acidification is then performed to separate and purify these organic acids. Due to this purification process, large amounts of neutralized salts are generated as by-products, and production costs increase as the production process becomes complicated. The high-cost burden of this purification processes acts as a factor that hinders the entry of fermented products into the chemicals market.

When microorganisms that shows high fermentation ability while being capable of growing even at low pH are used for the production of acidic substances such as organic acids in order to solve the above-described problems, processes of neutralizing the pH of media and performing acidification may be omitted, and thus it is possible to reduce costs through process simplification and reduction in the use of additives.

In many cases, however, the growth rate of microorganisms that survive at low pH is very low, and hence it is not possible to obtain a sufficient amount of cells required for the production of substances. Therefore, these microorganisms show a low consumption rate of raw materials, and thus are difficult to apply to industrial fermentation processes. Therefore, it is very important to select microorganisms that have the property of maintaining a high consumption rate of raw materials while growing rapidly at a pH lower than the pKa of the product.

These microorganisms can be selected from various strain libraries through various selection pressures. Examples of the selection pressures include resistance at the target product concentration, resistance to the raw material concentration, the consumption rates of raw materials, pH conditions, and the growth ability in minimal media. The selection of microorganisms can be performed manually, but when automated screening is performed, strains having excellent characteristics can be quickly selected from a larger number of subjects.

The selected microorganisms possess excellent properties of withstanding the selection pressures, but in most cases, they produce other products without producing a target product. Therefore, in order to impart the ability to produce the target product to the selected microorganisms, studies have been conducted to genetically introduce genes for conversion into the target product and to eliminate the ability to produce the products that are originally produced.

In order to impart the ability to produce the target product to the selected microorganisms, genes enabling conversion into the target product are introduced or a method of enhancing the genes originally contained in the microorganisms is used. However, in general, since the activities of the contained genes and the enzymes produced therefrom are often low, highly active exogenous genes are introduced in most cases. In addition, in this process, it is essential to introduce a promoter capable of strongly expressing exogenous DNA.

As to usable promoters, when a target microorganism is yeast, the promoter of *Saccharomyces cerevisiae*, a well-known yeast, may generally be used, and various genetic engineering techniques developed for *S. cerevisiae* may also be applied. In addition, strong promoters may be selected from promoters that are involved in the major carbon flux of selected microorganisms, and it is necessary to apply a method that can most effectively express the target gene through various techniques. In particular, for selected acid-resistant yeasts, when genetic engineering studies related to the yeasts have not been conducted, it is a common approach to use the promoter of *S. cerevisiae* or use the endogenous promoter of the selected microorganisms.

In general, promoters have various regulatory regions including a core promoter region in eukaryotic bacteria, and the regulatory genes are different between microorganisms. Therefore, it is possible to find an optimal region while confirming the role of the promoter by selecting a sequence having a sufficient length at the 5' end of the ORF, but a separate study is needed for remote control mechanisms (enhancer, silencer, etc.) or control mechanisms that work in combination.

Accordingly, the present inventors have made extensive efforts to find a promoter suitable for exogenous gene expression in order to select a yeast having resistance to an organic acid and impart the ability to produce useful substances to the yeast. As a result, the present inventors have found that, when a target gene is expressed using a promoter derived from an ethanol-producing metabolic pathway, expression of the target gene significantly increases, so that the production of the target product increases, thereby completing the present invention.

SUMMARY OF THE INVENTION

An object of the present invention is to provide a novel promoter derived from an organic acid-resistant yeast.

Another object of the present invention is to provide a recombinant vector containing the promoter, and a recombinant microorganism having the recombinant vector introduced therein.

Still another object of the present invention is to provide a gene construct in which the novel promoter and a gene encoding a target protein are operably linked to each other.

Yet another object of the present invention is to provide a method of producing an organic acid using a recombinant microorganism having introduced therein a recombinant vector containing the novel promoter and an organic acid production-related gene.

To achieve the above objects, the present invention provides a promoter comprising the nucleotide sequence of SEQ ID NO: 1 or SEQ ID NO: 2.

The present invention also provides a recombinant vector containing the promoter.

The present invention also provides a recombinant microorganism having the recombinant vector introduced therein.

The present invention also provides a method for producing an organic acid, the method comprising steps of: (a) producing the organic acid by culturing the recombinant microorganism having the recombinant vector introduced therein; and (b) collecting the produced organic acid.

The present invention also provides a gene construct in which a promoter comprising the nucleotide sequence comprising SEQ ID NO: 1 and a gene encoding a target gene are operably linked to each other.

The present invention also provides a recombinant microorganism having the gene construct introduced into the chromosome thereof.

The present invention also provides a method for producing an organic acid, the method comprising steps of: (a) producing the organic acid by culturing the recombinant microorganism having the gene construct introduced therein; and (b) collecting the produced organic acid.

The present invention also provides a recombinant strain obtained by deleting or inactivating g4423 gene in an acid-resistant yeast YBC strain (KCTC13508BP) and having reduced ethanol productivity.

The present invention also provides a recombinant microorganism for target gene overexpression in which a target gene is inserted downstream of the promoter of g4423 in the genome of a YBC strain (KCTC13508BP) and expression of the target gene is regulated by the promoter of g4423.

The present invention also provides a method for producing an organic acid, the method comprising steps of: (a) producing the organic acid by culturing the recombinant microorganism; and (b) collecting the produced organic acid.

The present invention also provides a method of overexpressing a target gene by culturing the recombinant microorganism.

BRIEF DESCRIPTION OF DRAWINGS

FIG. 1 shows examples of gene cassettes for expressing one, two or three 3-HP pathway enzymes. (a) is a general cassette for expressing one enzyme, (b) is a cassette for introducing MCRsa1 enzyme while using the g4423 promoter, (c) is a cassette for introducing LDH while using the g4423 promoter, (d) is a cassette for introducing three 3-HP producing enzymes (MCR, HPDH, and EUTE), and (e) a cassette for using a 1-kb g4423 promoter which is the promoter of MCR enzyme.

FIG. 2 shows examples of yeast expression plasmids for expressing one, two or three 3-HP pathway enzymes.

FIG. 3 shows the results of analyzing the expression levels of MCR genes (MCRsa1 and MCRsa2) in constructed recombinant strains containing the promoter of S. cerevisiae and the promoter (1 kb) of a YBC strain.

FIG. 4 shows the results of analyzing the expression levels of BDHcm gene, HPDHec gene and EUTEdz gene, which are other genes involved in 3-HP production, in recombinant strains containing an ScTEF1p promoter.

FIG. 5 shows the results of comparing the expression levels of MCR gene and 3-HP production-related genes in S. cerevisiae strains. In FIGS. 5, 995-1 and 995-3 show different phenotypes of the same genotype.

FIG. 6 shows the results of RT-qPCR performed to analyze the expression levels of seven ADH gene candidates selected through genetic information on S. cerevisiae.

FIG. 7 shows the results of analyzing glucose utilization (A) and ethanol production (B) in recombinant strains YBC-1563 from which g4423 gene was removed.

FIG. 8 shows the results of analyzing the expression levels of MCRsa1 in recombinant YBC strains in which g4423 gene is replaced with MCRsa1 gene.

FIG. 9 shows the results of analyzing expression of MCRsa1 gene in which g4423 promoter and terminator regions are located in a 1-kb truncated region.

FIG. 10 shows the results of analyzing the production of lactate in recombinant YBC strains in which three LDH genes are replaced with g4423.

DETAILED DESCRIPTION AND PREFERRED EMBODIMENTS OF THE INVENTION

Unless otherwise defined, all technical and scientific terms used in the present specification have the same meanings as commonly understood by those skilled in the art to which the present invention pertains. In general, the nomenclature used in the present specification is well known and commonly used in the art.

For a bioconversion process for the production of products, such as organic acids, which create an acidic environment, among various products, acid-resistant microorganisms, particularly microorganisms that show rapid growth even in an acidic environment and may maintain a high raw material absorption rate, are selected in order to reduce the complexity of the downstream process and the accompanying compound and facility investment costs. The selected microorganisms inherently have the ability to produce the target product in many cases, and thus it is necessary to develop a variety of genetic engineering tools in order to effectively impart the ability to produce the target product to the target microorganism.

A promoter is a regulatory region capable of strongly expressing an exogenous target gene or expressing the exogenous target gene according to conditions, and basically, it is necessary to select a promoter that can strongly express the target gene. Under glucose conditions, this strong promoter is generally selected from promoters involved in glycolysis or in the production of a major fermentation product by the microorganism.

Known strong promoters include, but are not necessarily limited to, TEF1, TPI1, HXT7, TDH3, PGK1, ADH1, and PYK1, and may differ between strains.

Common Crabtree-positive yeasts, including the microorganisms selected in the present invention, produce ethanol as a major fermentation product in many cases, and the promoters thereof are also strongly expressed and mostly work under favorable conditions for fermentation, that is, under conditions of high sugar concentration.

In particular, for promoters involved in ethanol metabolism, technology is often developed with the aim of blocking ethanol production while expressing exogenous genes. Thus, when the endogenous promoter of a strain is used, there is an advantage in that the effect of blocking ethanol production and the effect of strongly expressing exogenous genes can be simultaneously achieved.

In the present invention, to introduce an organic acid production-related gene with high efficiency in order to impart organic acid productivity to the acid-resistant yeast YBC (KCTC13508BP), a promoter suitable for this introduction was selected. In one example of the present invention, it was confirmed that, when MCR gene, which is a gene related to 3-hydroxypropionic acid (3-HP) production, was introduced using a promoter derived from *Saccharomyces cerevisiae* or the endogenous promoter of YBC, which has been used in a conventional art, the expression efficiency of the gene was significantly low. In another example of the present invention, it was confirmed that, when MCR gene was expressed using the promoter of g4423 that is the gene of the enzyme ADH involved in ethanol production, a high expression level of the gene and excellent 3-HP productivity were obtained.

Therefore, in one aspect, the present invention is directed to a promoter comprising the nucleotide sequence of SEQ ID NO: 1 or SEQ ID NO: 2.

The promoter of the present invention is strongly expressed in glucose culture and the logarithmic growth phase, and shows a good expression level even when cultured in an acidic medium. In addition, the promoter works well on yeast expression of heterologous genes, including yeast-derived genes, particularly Archaeal-derived genes and bacteria-derived genes. In particular, the promoter of the present invention is an essential promoter for producing various compounds in acid-resistant strains, and is a promoter capable of enhancing the expression of protein-encoding DNA influenced by the promoter, especially when the DNA is an organic acid-producing DNA. In addition, the promoter is a promoter that can be strongly expressed even in the presence of organic acids inside and outside cells.

In another aspect, the present invention is directed to a recombinant vector containing the promoter, and a recombinant microorganism having the recombinant vector introduced therein.

In the present invention, the recombinant vector may further contain a terminator comprising the sequence of SEQ ID NO: 3 or SEQ ID NO: 4.

In the present invention, the recombinant vector may further contain a gene encoding a target protein, and the target protein may be a protein that is involved in organic acid production.

In the present invention, it has been found that it is possible to produce 3-hydroxypropionic acid and lactic acid as the organic acids, but the present invention is not necessarily limited thereto.

Examples of organic acid production-related genes that are expressed using this promoter include genes encoding fumarate reductase, succinyl coA synthetase and phosphoenolpyruvate carboxylase in the succinic acid pathway (Progress of succinic acid production from renewable resources: Metabolic and fermentative strategies, Bioresource Technology 245(B); 1710-1717, 2017); genes encoding butyryl kinase, enoate reductase, adipyl coA transferase and adipate semialdehyde dehydrogenase in the adipic acid pathway (Development of a Platform Strain for Production of Adipic Acid Yields Insights into the Localized Redox Metabolism of *S. cerevisiae*, Patrick Hyland. A thesis of Master of Applied Science, Graduate Department of Chemical Engineering and Applied Chemistry, University of Toronto, 2013); a gene encoding methylmalonyl CoA reductase in the 3-hydroxyisobutyric acid pathway (Korean Patent Application No. 2016-0075640); genes encoding alpha-ketoisovalerate decarboxylase and potentially phenylacetaldehyde dehydrogenase in the isobutyric acid pathway (ChemSusChem 2011, 4, 1068-1070); a gene encoding malate dehydrogenase in the malic acid pathway (Malic Acid Production by *Saccharomyces cerevisiae*: Engineering of Pyruvate Carboxylation, Oxaloacetate Reduction, and Malate Export, Appl. Environ. Microbiol., 74: 2766-2777, 2008); and a gene encoding cis-aconitic acid decarboxylase in the itaconic acid pathway (Biochemistry of microbial itaconic acid production, Front Microbiol. 2013; 4: 23.). The promoter may be used for overexpression of the gene in the last step of each of the pathways, and this is also specified in the related prior art document (JP4700395B2). In addition, the promoter may also be applied to other genes of the same pathway, in addition to the genes exemplified above.

The promoter of the present invention is a polynucleotide that comprises the nucleotide sequence set forth in SEQ ID NO: 1 and has strong activity even under organic acid production conditions. In addition, sequences with mutations such as deletion or insertion in the nucleotide sequence of SEQ ID NO: 1 may exist due to the diploid nature of the YBC strain, and sequences including these mutated sequences can also exhibit the same characteristics (The Baker's Yeast Diploid Genome Is Remarkably Stable in Vegetative Growth and Meiosis, PLoS Genet 6(9):2010. Ploidy changes and genome stability in yeast, Yeast 31: 421-430, 2014).

In addition, the terminator, which acts together with the promoter of the present invention, comprises the nucleotide sequence set forth in SEQ ID NO: 3 or 4.

In the present invention, examples of the target protein include, but are not limited to, malonyl-CoA-reductase, lactate dehydrogenase, fumarate reductase, succinyl coA synthetase, phosphoenolpyruvate carboxylase, butyryl kinase, enoate reductase, adipyl coA transferase, adipate semialdehyde dehydrogenase, methylmalonyl CoA reductase, alpha-ketoisovalerate decarboxylase, potentially phenylacetaldehyde dehydrogenase, malate dehydrogenase, and cis-aconitic acid decarboxylase.

In the present invention, the recombinant is preferably yeast, more preferably the acid-resistance yeast YBC (KCTC13508BP).

In still another aspect, the present invention is also directed to a method for producing an organic acid, the method comprising steps of: (a) producing the organic acid by culturing the recombinant microorganism having the recombinant vector introduced therein; and (b) collecting the produced organic acid.

In yet another aspect, the present invention is directed to a gene construct in which a promoter comprising the nucleotide sequence comprising SEQ ID NO: 1 or SEQ ID NO: 2, and a gene encoding a target gene are operably linked to each other, and a recombinant microorganism having the gene construct introduced into the chromosome thereof.

In the present invention, the target protein may be a protein that is involved in organic acid production. The target protein may be selected from among malonyl-CoA-reductase, lactate dehydrogenase, and the like, but is not limited thereto, and any protein that is involved in organic acid production may be used without limitation.

In the present invention, the recombinant is preferably yeast, more preferably the acid-resistance yeast YBC (KCTC13508BP).

In yet another aspect, the present invention is directed to a method for producing an organic acid, the method comprising steps of: (a) producing the organic acid by culturing the recombinant microorganism having the gene construct introduced therein; and (b) collecting the produced organic acid.

The promoter of the present invention constitutes a DNA construct to be introduced into yeast together with a gene encoding the target protein. These DNA constructs include constructs suitable for various yeast transformation methods known to those skilled in the art, and examples of DNA constructs for homologous recombination are shown in SEQ ID NOs: 5 and 6. The DNA construct is a two-allele deletion cassette for deletion of the g4423 gene. In addition, when the target DNA is inserted into this cassette, a gene insertion cassette for each allele is produced, which is well known to researchers skilled in the art.

In the present invention, the cassette may be comprising the nucleotide sequence of SEQ ID NO: 5 or SEQ ID NO: 6, and the cassette may contain a target gene.

In a further aspect, the present invention is directed to a method for overexpressing a target gene, the method comprising replacing the g4423 gene in the genome of the YBC strain (KCTC13508BP) with the target gene.

In another aspect, the present invention is directed to a recombinant microorganism for target gene overexpression in which a target gene is inserted downstream of the promoter of g4423 in the genome of the YBC strain (KCTC13508BP) and expression of the target gene is regulated by the promoter of g4423.

In yet another aspect, the present invention is directed to a method for producing an organic acid, the method comprising steps of: (a) producing the organic acid by culturing the recombinant microorganism; and (b) collecting the produced organic acid.

In yet another aspect, the present invention is directed to a method of overexpressing a target gene by culturing the recombinant microorganism.

In yet another aspect, the present invention is directed to a recombinant strain obtained by deleting or inactivating the g4423 gene in the acid-resistant yeast YBC strain (KCTC13508BP) and having reduced ethanol productivity.

As used herein, "homology" refers to the percent identity between two amino acid or polynucleotide moieties for comparison. The term "similarity" refers to the degree to which two amino acid or polynucleotide sequences are functionally or structurally identical to each other as determined by the comparison window. The sequence homology or similarity can be determined by comparing sequences using the standard software, for example, a program called BLASTN or BLASTX, developed based on BLAST (Proc. Natl. Acad. Sci. USA, 90, 5873-5877, 1993).

The g4423 promoter may preferably have a sequence showing a sequence homology of 90% or more, 92% or more, 93% or more, 95% or more, 97% or more, 98% or more, 99% or more, or 100% to the sequence of SEQ ID NO: 1.

If any promotor exhibits an equivalent level of expression efficiency while having a homology of 90% or more to the g4423 promoter of the present invention, it can be considered a substantially equivalent promoter.

In some cases, the g4423 promoter according to the present invention may be mutated using techniques known in the art in order to increase the expression efficiency of the target gene.

In the present invention, the recombinant yeast may have acid resistance. In order to produce an acid-resistant recombinant yeast suitable for the present invention, a host yeast having resistance to organic acids is preferably used.

The acid-resistant yeast may be an acid-resistant yeast selected from the group consisting of the genus *Saccharomyces, Kazachstania saccharomyces* and the genus *Candida*. For example, the acid-resistant yeast may be selected from the group consisting of *Saccharomyces cerevisiae, Kazachstania exigua, Kazachstania bulderi*, and *Candida humilis*, but is not limited thereto.

"Acid-resistant yeast" refers to a yeast having resistance to an organic acid such as 3-HP or lactic acid, and acid resistance can be determined by evaluating growth in media containing various concentrations of organic acid. In other words, "acid-resistant yeast" refers to yeast that has a higher growth rate and biomass consumption rate compared to general yeast in media containing a high concentration of organic acid.

In the present invention, the term "acid-resistant yeast" is defined as a yeast that can maintain a biomass consumption rate (sugar consumption rate, etc.) of at least 10% or a specific growth rate of at least 10% at a pH lower than the pKa value of the organic acid in a medium containing 1 M or more of organic acid compared to a medium containing no organic acid. More specifically, in the present invention, the term "acid-resistant yeast" is defined as a yeast that can maintain a biomass consumption rate (sugar consumption rate, etc.) of at least 10% or a specific growth rate of at least 10% at a pH of 2 to 4 compared to a pH of 7.

The recombinant yeast according to the present invention may be produced according to a conventional method by inserting the gene into the chromosome of the host yeast or by introducing a vector containing the gene into the host yeast.

As the host yeast, a host cell into which DNA is introduced with high efficiency and in which the introduced DNA is expressed with high efficiency is commonly used. Although an acid-resistant yeast was used in one example of the present invention, but the present invention is not limited thereto, any type of yeast may be used as long as a target DNA may be sufficiently expressed therein.

The recombinant yeast may be produced according to any transformation method. "Transformation" refers to a process of introducing DNA into a host cell and making the DNA replicable therein as a chromosomal factor or by completion of chromosomal integration, which is a phenomenon of artificially causing a genetic change by introducing exogenous DNA into a cell. Typical transformation methods include electroporation, a lithium acetate-PEG method, and the like.

In addition, in the present invention, any commonly known genetic engineering method may be used as a method of inserting a gene into the chromosome of a host microorganism. Examples of the method include methods that use a retroviral vector, an adenovirus vector, an adeno-associated virus vector, a herpes simplex virus vector, a poxvirus vector, a lentiviral vector, a non-viral vector, or the like. "Vector" refers to a DNA construct containing a DNA sequence operably linked to a suitable control sequence capable of expressing the DNA in a suitable host. The vector may be a plasmid, a phage particle, or simply a potential genomic insert. Once transformed into a suitable host, the vector may replicate and function independently of the host genome, or may, in some cases, integrate into the genome itself. Plasmid is currently the most commonly used form of vector, and linearized DNA is also a form that is commonly used for integration into the genome of yeast.

A typical plasmid vector has a structure comprising: (a) a replication origin that allows replication to occur efficiently such that plasmid vectors per host cell are created; (b) an antibiotic-resistance gene or an auxotrophic marker gene that allows a host cell transformed with a plasmid vector to be selected; and (c) restriction enzyme digestion sites into which foreign DNA fragments may be inserted. Even if there is no suitable restriction site of a restriction enzyme, a vector and foreign DNA may be easily ligated when using the linker or the synthetic oligonucleotide adaptor according to a general method. Even if suitable restriction enzyme digestion sites are not present in the vector, the use of a synthetic oligonucleotide adaptor or linker according to a conventional method enables foreign DNA fragments to be easily ligated with the vector.

In addition, the gene is "operably linked" when placed in a functional relationship with another nucleic acid sequence. This can be a gene and regulatory sequence(s) which are connected in such a way as to permit gene expression when the appropriate molecules (e.g., transcriptional activator proteins) are bound to the regulatory sequences(s). For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects transcription of the sequence; or a ribosome binding site is operably linked to a coding sequence if it is positioned so as to facilitate translation.

Generally, "operably linked" means that the DNA sequences being linked are contiguous and, in the case of a secretory leader, are contiguous and in reading phase. However, enhancers do not have to be contiguous. Linking is accomplished by ligation at convenient restriction enzyme sites. If such sites do not exist, a synthetic oligonucleotide adaptor or linker is used in accordance with a conventional method.

It is well understood that not all vectors function equally in expressing the DNA sequence of the present invention, likewise, not all hosts are equally suitable for hosting an identical expression vector. However, those skilled in the art are able to make a suitable selection from other various vectors, expression regulatory sequences and hosts without undue experimentation without departing from the scope of the present invention. For example, a vector may be selected taking into consideration the host cell since the vector should be replicated in the host cell. In addition, the copy number of a vector, the ability to control the copy number, expression of another protein (e.g., an antibiotic marker) encoded by the gene in the vector should also be considered.

A carbon source that is used in the present invention may be one or more selected from the group consisting of glucose, xylose, arabinose, sucrose, fructose, cellulose, galactose, glucose oligomers and glycerol, but is limited thereto.

In the present invention, culture may be performed under conditions in which microorganisms, such as *E. coli*, no longer act (e.g., cannot produce metabolites). For example, the culture may be performed at a pH of 1.0 to 6.5, preferably 1.0 to 6.0, more preferably 2.6 to 4.0, but is not limited thereto.

Hereinafter, the present invention will be described in more detail with reference to examples. These examples are only to illustrate the present invention, and it will be apparent to those of ordinary skill in the art that the scope of the present invention is not construed as being limited by these examples.

Example 1: Analysis of Expression Pattern of Malonyl-CoA Reductase (MCR) Using Conventional Promoter in YBC Strain Selection of Acid-Resistant Strain The present inventors selected a group of strains having acid resistance through a test for various yeast strains (Korean Patent Application Publication No. 2017-0025315). For the selected yeast strains, lactic acid was added to the medium at the beginning of culture, and the strain having the best acid resistance was selected while checking the growth and sugar consumption rates of the microorganisms. At this time, an inoculum OD value of 4 and a YP medium (20 g/L peptone and 10 g/L yeast extract) supplemented with 3.5% glucose were used, and the experiment was performed with a 50-ml flask culture under conditions of 30° C. and 100 rpm. The lactic acid concentration at the beginning of culture varied from 0 to 80 g/L. The results were compared and analyzed, and a YBC strain having the best acid resistance was selected.

The YBC strain (*Kazachstania exigua* sB-018c) was deposited in the Korea Research Institute of Bioscience and Biotechnology Biological Resource Center, a depository institution, on Apr. 11, 2018 under accession number KCTC13508BP.

MCR Expression Using Conventional Promoter in Acid-Resistant Strain YBC

In this Example, a gene encoding MCR (malonyl-CoA reductase), an enzyme involved in 3-HP (3-hydroxypropionic acid) production, was expressed in the YBC strain.

The malonyl-CoA pathway that produces 3-HP is a metabolic pathway in which acetyl-CoA is converted to malonyl-CoA through carboxylation and then converted to 3-HP through a reduction reaction (acetyl-CoA→malonyl-CoA→3-HP). The malonyl-CoA pathway has been studied the most as a 3-HP production pathway, because intermediates commonly produced by microorganisms including *E. coli* pass through this pathway (US Patent Application Publication No. US 2013/0071893 A1). Malonyl-CoA can be converted into 3-HP by the action of malonate reductase and 3-HP dehydrogenase, and thus a method of converting malonyl-CoA to 3-HP using recombinant *E. coli* in the presence of glucose or glycerol is well known.

In this Example, the experiment was conducted on MCRsa1 and MCRsa2, which are highly efficient genes among known MCR genes. The MCRsa1 and MCRsa2 used were synthesized using yeast codon usage based on data from Genbank, and the information on the MCR genes used in this Example is shown in Table 1 below.

TABLE 1

| Gene | GenBank Accession No. | GI No. | Organism | Abbreviation |
|---|---|---|---|---|
| | WP_020198954.1 | 519043079 | Sulfolobales archaeon AcdI | MCRsa1 |
| SacRon12I_11780 | AGE74568.1 | 449039143 | Sulfolobus acidocaldarius Ron12/I | MCRsa2 |

In order to introduce the gene into the YBC strain, a cassette shown in FIG. 1(a) was constructed.

The cassette was constructed to have an antibiotic resistance gene. For targeting the target gene, the 5' UTR and 3' UTR regions of the target gene were designed to have the restriction enzyme sites shown in FIG. 1 on the basis of the full genome sequence or the partial genome sequence, and then subjected to PCR. The promoter and terminator derived from S. cerevisiae were constructed based on known genetic information (for example, Saccharomyces Genome Database). As the antibiotic resistance gene, HygR was used as an example in FIG. 1(a). However, other antibiotic resistance genes for eukaryotes may be used for the strain, and these genes may be easily constructed by any person skilled in the art. Since the antibiotic resistance gene needs to be removed after use so that genetic manipulation in the next step can be performed, sites (lox71 and lox66) for Cre-loxp at both ends were introduced. In addition, the promoter and terminator derived from the YBC strain were constructed using the same method as the method of extracting the UTR region. When a plurality of target genes is to be expressed, a cassette capable of expressing the plurality of genes as shown in FIG. 1(d) was constructed, and the UTR, the ORF gene and antibiotic resistance gene were constructed by exchange using the restriction enzyme located at the end of each region so as to suit the purpose.

For Donor DNA, a plasmid containing a cassette was cleaved using restriction enzymes or amplified by PCR, and regions of each gene can be exchanged using a restriction enzyme located at each end. In addition to the method that uses the restriction enzymes, a cassette was also constructed using Gibson assembly. For how to use this Gibson assembly, a number of products and usages are well known. In this Example, the cassette was constructed using NEB Gibson assembly master mix and cloning kit. Thereamong, oligomers related to MCR and G4423 are shown in Table 2 below.

TABLE 2

| Name | SEQ ID NO | Sequence | Description |
|---|---|---|---|
| oSK-1125 | 9 | CTTCAAAGTTCTTCTCATTTTGTTGTCGACTT TTGTTTATAATTTATCAAATATGTTGATT | keFBA1p MCRsa1 GA |
| oSK-1126 | 10 | GTCGACAACAAAATGAGAAGAAC | MCRsa1 GA |
| oSK-1127 | 11 | CTTTCAAGACTCTTCTCATTTTGTTGTCGACT TTGTTTATAATTTATCAAATATGTTGATT | keFBA1p MCRsa2 GA |
| oSK-1130 | 12 | GTCGACAACAAAATGAGAAGAGTC | MCRsa2 GA |
| oSK-1220 | 13 | TACGACTCACTATAGGGCGAATTGCCTGCA GGGTTAACTCAGTTTTCTCTCTTTCCC | ADH1ke (g4423) GA |
| oSK-1221 | 14 | ACTAGAGCTCCCTCGGACGTGGGCCCTTTTA AATGATTTTTATTTGTATTGATATATGG | ADH1ke (g4423) GA |
| oSK-1222 | 15 | GGGCCCACGTCCGAGGGAGCTCTAGTACCT CGGCGATCGCTTTGTCTTTATTTTTGAAATG TTAATAGTC | ADH1ke (g4423) GA |
| oSK-1223 | 16 | TAACCCTCACTAAAGGGAACAAAAGCTGGG CGCGCCCTTTTGCAGTTGCGGATTTC | ADH1ke (g4423) GA |
| oSK-1358 | 17 | GGTTACATCCCTAAGTGAATCGATGGAGAT TGATAAGACTTTTC | MCRsa1 - TEF1t GA fwd |
| oSK-1359 | 18 | CAAAAGTCGACAACAAAATGAGAAGAACTT TGAAGGCTGC | keFBAp-MCRsa1 GA fwd |
| oSK-1360 | 19 | CTTCAAAGTTCTTCTCATTTTGTTGTCGACTT TTGTTTATAATTTATTGAAATATGTTG | keFBAp-MCRsa1 GA rev |
| oSK-1412 | 20 | CTGTAGCACCTAAAATGGCAGCCTTCAAAG TTCTTCTCATTTTAAATGATTTTTATTTGTA TTGATATATGGATATATATGTGTACGG | g4423 promoter rev + MCRsa1 flank |
| oSK-1413 | 21 | GGTTACATCCCTAAGTGAGTCATTTAATTTA TTCTTTTAGAATATAATTATTTTGTCTTTATT TTTGAAATGTTAATAGTCTTTTTTTT | g4423 terminator forw + MCRsa1 flank |

TABLE 2-continued

| Name | SEQ ID NO | Sequence | Description |
|---|---|---|---|
| oSK-1414 | 22 | CCGTACACATATATATCCATATATCAATACA AATAAAAATCATTTAAAAATGAGAAGAACT TTGAAGGCTGCCATTTTAGG | MCRsa1 forw + g4423 flank |
| oSK-1415 | 23 | ATTTCAAAAATAAAGACAAAATAATTATAT TCTAAAAGAATAAATTAAATGACTCACTTA GGGATGTAACCCTTTTCGATCAAATATTC | MCRsa1 rev + g4423 flank |
| oSK-1416 | 24 | AAATTCGGGCCCGTTAACTCAGTTTTCTCTC TTTCCCTCCACC | g4423 promoter forw + ApaI restriction site |
| oSK-1417 | 25 | TTTGTTGTCGACTTTTAAATGATTTTTATTTG TATTGATATATGGATATATATGTGTACGG | g4423 promoter rev + SalI restriction site |
| oSK-1418 | 26 | TGCTACCTTAATTTCTCATGGAAAGTGGCA | g4423 promoter forw |
| oSK-1419 | 27 | GTTAACGAGTTTAATGTTTAAAAGCGTATAT AAG | g4423 terminator rev |
| oSK-1621 | 28 | TAATCTCACCGTACACATATATATCCATATA TCAATACAAATAAAAATCATTTAAAAATGA GAAGAGTCTTGAAAGCAGCAATCTTGG | MCRsa2 + g4423p flank |
| oSK-1622 | 29 | GTGGAACCCAAGATTGCTGCTTTCAAGACT CTTCTCATTTTTAAATGATTTTTATTTGTATT GATATATGGATATATATGTGTACGG | g4423p + MCRsa2 flank |
| oSK-1623 | 30 | TGGTATTTTGGCAACAGAATTTTTGGTTGAA AAGGGTTACATGGATTGATTTGTCTTTATTT TTGAAATGTTAATAGTCTTTTTTTT | g4423t + MCRsa2 flank |
| oSK-1624 | 31 | TTTGTTCAAAGTAAAAAAAAAGACTATTA ACATTTCAAAAATAAAGACAAATCAATCCA TGTAACCCTTTTCAACCAAAAATTCTG | MCRsa2 + g4423t flank |

In the case of the acid-resistant S. cerevisiae strain, expression was performed using the cassette or the expression plasmid shown in FIG. 2 (pSK-084 and/or pSK-085) (FIG. 2).

To introduce the constructed cassette into the YBC strain, a linearized donor DNA was constructed by PCR or a restriction enzyme method and then introduced using an electroporation method or a lithium acetate method, as in general yeast transformation. Next, selection was performed using a medium according to the auxotroph marker or antibiotic marker used. Through the colonies selected from the selection medium, whether the gene was introduced into the correct locus of the chromosome was confirmed by colony PCR either using the gene ORF primers into which the target is to be introduced and using the primers of the introduced gene. Subsequently, genomic DNA was extracted from the cultured cells, and the correct genotype was determined.

These constructed strains were each cultured (30° C. and 250 rpm) in a 250-mL flask using 20-mL selective SC-based medium (20 g/L of glucose) or YPD medium, and culture was continued until glucose and ethanol were completely consumed.

Table 3 below shows recombinant strains which were constructed by the above-described method and into which the MCR gene was introduced together with a Saccharomyces cerevisiae-derived promoter (TEFL) and a YBC strain-derived promoter (FBA1p).

TABLE 3

| Strain | Description |
|---|---|
| S.c wt | S. cerevisiae wt (acid tolerant) |
| S-995 | S. cerevisiae Acs2Δ-HygR::TEF1p-MCRsa2-TEF1t: TDH3p-HPDH-TDH3t: PDC1p-EutE-PDC1t |
| YBC-001 | YBC wt |
| YBC -061 | acs2Δ-TEF1p-MCRsa1-TEF1t: TDH3p-BDH-TDH3t: PDC1p-EutE-PDC1t-(NatR) |
| YBC -062 | ald2Δ-TEF1p-MCRsa1-TEF1t: TDH3p-BDH-TDH3t: PDC1p-EutE-PDC1t |
| YBC -067 | ald2Δ-TEF1p-MCRsa1-TEF1t: TDH3p-BDH-TDH3t: PDC1p-EutE-PDC1t |
| YBC -068 | ald2Δ-TEF1p-MCRsa1-TEF1t: TDH3p-BDH-TDH3t: PDC1p-EutE-PDC1t |
| YBC -1178 | ald2Δ-NAT::TEF1p-MCRsa2-TEF1t: TDH3p-HPDH-TDH3t: PDC1p-EutE-PDC1t |
| YBC -1413 | ald2Δ-NAT::YBC-FBA1p-MCRsa2-TEF1t: YBC-TPI1p-HPDH-TDH3t: YBC-TDH3p-EutE-PDC1t |
| YBC -1497 | ald2Δ-TEF1p-MCRsa2-TEF1t: TDH3p-HPDH-TDH3t: PDC1p-EutE-PDC1t |

The recombinant strains were each cultured (30° C. and 250 rpm) in a 250-mL flask using 20-mL YPD medium (20 g/L peptone, 10 g/L yeast extract, and 20 g/L dextrose). The cells were collected at the time of ethanol production and the time of ethanol consumption, and then RT-qPCR was performed on the MCR gene.

The RT-qPCR method used in this Example was as follows. After extracting RNA during exponential growth of the target strain, cDNA was produced using the RNA as a template. An oligomer specific to each of the target gene and the housekeeping gene (used as the Ref gene) was synthesized, and qPCR was performed using the oligomer. The gene used in this Experiment was ALG9, and the size of the fragment amplified with the primers used was 147±3 bp.

Table 4 below shows the qPCR primers used in the experiment and the primers used in the following Examples.

TABLE 4

Primers for qPCR

| Name | SEQ ID NO | Sequence | Description |
| --- | --- | --- | --- |
| oSK-1318 | 32 | CGGACTTTAGAGCCTTGTAGAC | g4423 qPCR fwd |
| oSK-1319 | 33 | ATCTGGTTACACTCACGATGG | g4423 qPCR rev |
| oSK-1320 | 34 | CCAAGTACGTTAGAGCTAACGG | g4423 qPCR 2 fwd |
| oSK-1321 | 35 | GAGCTTCTCTGGTATCAGCT | g4423 qPCR 2 rev |
| oSK-1322 | 36 | AGCTTTAGCAAACATTAGACCC | g1044 qPCR fwd |
| oSK-1323 | 37 | ATTCCATCCGAATATGCTGGT | g1044 qPCR rev |
| oSK-1324 | 38 | GGAACCTAAATGACTGTTGGCA | g1044 qPCR 2 fwd |
| oSK-1325 | 39 | AGGATGTTGATTTCGACTCGT | g1044 qPCR 2 rev |
| oSK-1326 | 40 | TTCCAAAGGGTACCAATTTAGCTG | g2289 qPCR fwd |
| oSK-1327 | 41 | GTACCGCTAATGAACCTAAACCA | g2289 qPCR rev |
| oSK-1328 | 42 | AGAGCTGACACTAGAGAAGCC | g2289 qPCR 2 fwd |
| oSK-1329 | 43 | GATGTGTCTACGACGTATCTACC | g2289 qPCR 2 rev |
| oSK-1330 | 44 | GTACTGGTAACGTCCAAGTC | g4117 qPCR fwd |
| oSK-1331 | 45 | GAACCCTTCCATACTCTACCA | g4117 qPCR rev |
| oSK-1332 | 46 | TTCAGTTCGTGCTACTCAAGG | g4117 qPCR 2 fwd |
| oSK-1333 | 47 | TCAATTGCAACGACAGAGAC | g4117 qPCR 2 rev |
| oSK-1334 | 48 | CCGTACCCTGAAGAGTTTACTG | g2807 qPCR fwd |
| oSK-1335 | 49 | CAACCATAGATTCACGAATTGCTC | g2807 qPCR rev |
| oSK-1336 | 50 | AGTGGATTTGGATTAATGGGTG | g2807 qPCR 2 fwd |
| oSK-1337 | 51 | GCTTCTGTAACACCTTTAACAC | g2807 qPCR 2 rev |
| oSK-1338 | 52 | AAATTGGTGACCGTGTTGGT | g727 qPCR fwd |
| oSK-1339 | 53 | AACCACCTTTACTACGGTAACCA | g727 qPCR rev |
| oSK-1340 | 54 | TTTAGTCGTCATCTGTTCAGGT | g727 qPCR 2 fwd |
| oSK-1341 | 55 | GAGACACCTAACAAACCAAATGG | g727 qPCR 2 rev |
| oSK-1342 | 56 | GATTCAAGCTTCTTCTCGTATCGG | g3610 qPCR fwd (ALG9 homolog) |
| oSK-1343 | 57 | GGAAATGATACCATTCACGACCT | g3610 qPCR rev (ALG9-homolog) |
| oSK-1350 | 58 | GTTCCGTCAAAGAAATCAAGCA | g5126 qPCR fwd |
| oSK-1351 | 59 | TGGTAAACCTGTATCTGACATCAC | g5126 qPCR rev |
| oSK-1352 | 60 | TTTAGTTGTCATTTGTGCCGGT | g5126 qPCR 2 fwd |
| oSK-1353 | 61 | GACACCTAACAAACCAAACGGA | g5126 qPCR 2 rev |
| oSK-1362 | 62 | GCTAACTTCAAAGGTGAACCTC | MCRsa1 qPCR fwd |
| oSK-1363 | 63 | AATCTACCAACTACGACGGAC | MCRsa1 qPCR rev |
| oSK-1364 | 64 | CAGATTCGAACCAGATATCCCT | MCRsa2 qPCR fwd |
| oSK-1365 | 65 | CCAATGGTAACAATACACCTTGAG | MCRsa2 qPCR rev |
| oSK-1382 | 66 | GGTAAAGCTTACTCAGAAGTTGTC | MCRsa1 qPCR 2 fwd |

TABLE 4-continued

Primers for qPCR

| Name | SEQ ID NO | Sequence | Description |
|---|---|---|---|
| oSK-1383 | 67 | CAGCACCTTGAGGTAATGGA | MCRsa1 qPCR 2 rev |
| oSK-1384 | 68 | CTATGCAAGCTGTTTCCGGT | MCRsa2 qPCR 2 fwd |
| oSK-1385 | 69 | CGTTGACGTTTCTCTTAGTTTCAG | MCRsa2 qPCR 2 rev |
| oSK-1386 | 70 | CTTTGAGTGCAAGTATCGCC | ALG9 qPCR fwd |
| oSK-1387 | 71 | TGTGTAATTGTTCACCAAAGCC | ALG9 qPCR rev |

As a result, as shown in FIG. 3, it was confirmed that the MCR genes (MCRsa1 and MCRsa2) were expressed in the recombinant strains constructed using the acid-resistant strain YBC. The levels of the genes expressed using the promoter of Saccharomyces cerevisiae and the promoter (1 kb) of the YBC strain were analyzed, and as a result, it was shown that the expression levels of the genes were not high or rather low compared to that of the Ref gene in qPCR. In addition, it was confirmed that the level of MCRsa2 expressed using the 1-kb FBA promoter (YBC FBA1p) derived from the YBC strain was lower than the level of MCRsa2 expressed using the ScTEF1p promoter (YBC-1413 in FIG. 3B).

In addition, the analysis of expression was also performed on BDHcm gene, HPDHec gene and EUTEdz gene, which are other genes involved in 3-HP production, in the recombinant strains YBC-061, YBC-062, YBC-067 and YBC-068 containing the ScTEF1p promoter.

As a result, as shown in FIG. 4, it was confirmed that, similarly to the MCR gene, the expression levels of these genes expressed using the ScTEF1p promoter were lower than the expression levels of the genes expressed using the endogenous promoter FBA1p of the YBC strain and the Saccharomyces cerevisiae-derived promoter (TEF1).

In addition, the production of 3-HP by the recombinant strain was also very low, and the production of 3-HP by the recombinant strain (in which the expression levels of three genes (MCRsa2, HPDH and EUTE) all increased) containing two copies of the gene was rather lower than the production of 3-HP by the YBC-1178 strain.

Example 2: Analysis of 3-HP Productivities by MCR Gene and Related Genes Expressed by Conventional Promoter The 3-HP productivities of the recombinant strains constructed in Example 1 were analyzed.

First, each of the recombinant strains was cultured with 25 mL of a YPD medium (20 g/L peptone, 10 g/L yeast extract, and 20 g/L dextrose) in a shake flask at 250 rpm and 30° C., and 15 µM of cerulenin (Sigma-Aldrich, USA) was added. Cerulenin functions to facilitate the production of 3-HP by inhibiting lipid synthesis from the carboxylation of cytosolic acetyl-CoA to malonyl-CoA. After each recombinant strain was cultured under the above culture conditions until the glucose was completely consumed, the cell density was measured and the production amounts of main metabolites including 3-HP in the culture medium were analyzed. In addition, culture was also performed under changed concentration, medium and culture conditions for specific conditions, but was not specifically described.

For analysis of 3-HP in the cell culture supernatant, a culture supernatant sample was analyzed using a Waters Alliance e2695 HPLC system (Waters, Milford, USA) with an injection volume of 10 µl. In HPLC, an Aminex HPX-87H organic acid column (300 mm×7.8 mm) (Bio-Rad, USA) connected to a fast acid analysis column (100 mm×7.8 mm) (Bio-Rad, USA) was used in the stationary phase. The column was maintained at +55° C., and 5.0 mM $H_2SO_4$ (Merck KgaA, Germany) was used as an eluent at a flow rate of 0.3 or 0.5 ml/min.

For detection of 3-hydroxypropionic acid, glucose, acetate, succinate, pyruvate, glycerol and ethanol, a Waters 2489 dual wavelength UV (210 nm) detector (Waters, Milford, USA) and a Waters 2414 differential refractometer (Waters, Milford, USA) were used.

As a result, as shown in Table 5 below, it was confirmed that all the recombinant strains showed low 3-HP productivity. From this low productivity, it was determined that the expression efficiency of major genes, particularly MCR, had a great influence on the production of 3-HP.

TABLE 5

Production of 3-HP in recombinant YBC strains

| Strain name | YBC-1178-1 | YBC-1178-3 | YBC1497-1 | YBC-1413-1 | YBC-1413-4 |
|---|---|---|---|---|---|
| 3-HP concentration (mg/L) | 16.4 | 8.5 | 8.1 | 1.8 | 1.6 |

Example 3: Analysis of Expression Efficiency of MCR Gene in S. cerevisiae

In order to compare the expression efficiency of MCR gene and related genes in the S. cerevisiae strain in which genetic information and gene tools are well set-up, the expression levels of 3-HP-producing genes, especially the MCR gene with low expression efficiency, were analyzed by the RT-qPCR method described in Example 1.

As a result, as shown in FIG. 5, it was confirmed that the expression level of the MCRsa2 gene was low even in the recombinant strains containing the endogenous promoter of S. cerevisiae. Thus, it was confirmed that it was necessary to select a novel promoter capable of increasing expression of the MCR gene.

Example 4: Analysis of Expression of Alcohol-Producing Gene in YBC Strain

In this Example, in order to select a promoter capable of increasing the expression of an exogenous gene in the YBC strain, a promoter that regulates the expression of a gene having high expression efficiency in the YBC strain itself was used, and the gene was replaced with an exogenous gene to be expressed.

From glycolysis- and ethanol production-related genes which are strongly expressed in the presence of glucose, genes which are highly efficient without influencing growth when replaced with other genes were selected, and a promoter that regulates expression of ADH (alcohol dehydrogenase) gene was targeted.

In particular, in order not to directly affect microbial growth, glycolysis-related genes should be eliminated. If the glycolysis-related genes are deleted or inactivated, the production of pyruvate, which is important for microbial growth, is inhibited or a problem occurs in the balance of the chain reaction, and thus the growth properties of microorganisms are adversely affected, resulting in a decrease in the fermentation ability. For this reason, when the target strain is an ethanol-producing strain, the PDC (pyruvate dehydrogenase complex) gene or the ADH gene is selected as the endogenous gene to be replaced, and PDC is used as an important pathway to produce a target compound in the target strain. For this reason, the ADH gene was selected as the gene to be deleted.

Strains with strong ethanol fermentation ability, such as yeast, have ADHs having a wide variety of strengths and functions. In order to identify major ethanol-producing ADHs among yeast ADHs and to select and use the corresponding promoter, several candidate genes were identified by comparing genome information on the YBC strain with known information on the ADH gene of S. cerevisiae and subjected to qPCR.

Seven ADH gene candidates were selected using bioinformatics information from the genome-wide sequence data of S. cerevisiae (see Table 6), and oligomers specific to the selected genes were designed and subjected to RT-qPCR (See Table 4 for primer sequences).

TABLE 6

| S. cerevisiae gene | Homolog in YBC | Identity-% (protein) | Genomic location* | Targeting signal |
|---|---|---|---|---|
| ADH1 | g4423 | 89.1% | ADH5 | no |
| ADH2 | g4423 | 77.2% | ADH5 | no |
| ADH3 | g2289 | 80.4% | ADH3 | mitochondrial |
| ADH4 | No homologs | | | |
| ADH5 | g4423 | 74.4% | ADH5 | no |
| SFA1 | g4117 | 79.5% | SFA1 | |
| ADH6 | g5126 | 63.4% | — | no |
|  | g1044 | 64.1% | — | no |
|  | g4395 | 64.0% | — | no |
|  | g727 | 63.7% | — | no |
|  | g2807 | 60.4% | — | no |
| ADH7 | g5126 | 63.0% | — | no |
|  | g1044 | 60.0% | — | no |
|  | g4395 | 61.8% | — | no |
|  | g727 | 62.1% | — | no |
|  | g2807 | 58.0% | — | no |

*Genes having similar gene sequences in YBC compared to S. cerevisiae genome

As a result, as shown in FIG. 6, it was confirmed that the expression level of the g4423 gene was significantly high.

A strain (YBC-1563) from which the g4423 gene was removed was constructed. Based on information on g4423 and UTR, a gene cassette similar to FIG. 1(a) was constructed, from which the g4423 ORF was removed and which had 5' and 3' UTRs and an antibiotic marker. The constructed gene cassette was used as donor DNA. For construction of the donor DNA, the cloning method using restriction enzymes as described above and the method using Gibson assembly were used. The constructed donor DNA was introduced, and the colonies grown in the plate corresponding to the marker gene were analyzed using ORF primers (forward primer (SEQ ID NO: 72): GAGA-TAGCACACCATTCACCA, and reverse primer (SEQ ID NO: 73): CAACGTT72AAGTACTCTGGTGTTTG) for identifying g4423. As a result, it was confirmed that the ORF was removed.

The strain was cultured with 50 ml of a medium (containing 40 g/L glucose) in a 250 ml flask at 30° C. and 250 rpm with a starting OD value of 0.7 until sugar and ethanol were completely consumed. Then, glucose consumption and ethanol production were analyzed. As a result, it was confirmed that ethanol production was reduced by 50% or more (FIG. 7).

Example 5: Analysis of Expression Level of YBC Recombinant Constructed by Replacing g4423 Gene with MCR Gene In order to use the strong expression ability of the g4423 gene identified in Example 4, the recombinant strain YBC-1684 was constructed by replacing the g4423 gene in the genome of the YBC strain with the MCRsa1 gene, and the expression level of the MCRsa1 gene was analyzed. Based on information on g4423 and UTR, the gene cassette of FIG. 1(b) was constructed, from which the g4423 ORF was removed and which had 5' and 3' UTRs and an antibiotic marker. In addition, an MCRsa1 sequence optimized for yeast codon usage was introduced into the ORF site of g4423. The constructed gene cassette was used as donor DNA. For construction of the donor DNA, the cloning method using restriction enzymes as described above and the method using Gibson assembly were used. The plasmid (pSK863) used in the donor DNA is set forth in SEQ ID NO: 7.

The donor DNA in the constructed cassette was amplified and introduced into the YBC strain. The grown colonies were analyzed using the following primers for identifying the g4423 ORF. As a result, it was confirmed that the g4423 ORF was removed and the MCRsa1 ORF existed, suggesting that MCRsa1 was introduced.

Forward primer (SEQ ID NO: 74) for analysis:
ATGAGAAGAACTTTGAAGGCTG,

Reverse primer (SEQ ID NO: 75):
TTACTTAGGGATGTAACCCTTTTCGA)

The strain was cultured with 50 ml of a medium (containing 40 g/L glucose) in a 250 ml flask at 30° C. and 250 rpm with a starting OD value of 0.7 until sugar and ethanol were completely consumed. Then, the amount of 3-HP and the amounts of sugar and ethanol produced were analyzed. RT-qPCR for analyzing the gene expression level was performed under the same conditions as those in Example 1, and the culture medium was sampled during the logarithmic growth phase. Table 7 below shows the specific genotypes of the constructed recombinant YBC strains.

TABLE 7

Recombinant YBC strains constructed by replacing g4423 gene with MCRsa1 gene

| Strain | Description |
|---|---|
| YBC-061 | acs2Δ(1/2)-TEF1p-MCRsa1-TEF1t: TDH3p-BDH-TDH3t: PDC1p-EutE-PDC1t-(NatR) |
| YBC-1684 | g4423::MCRsa1 |
| YBC-Trans | g4423::MCRsa1, ald2Δ-FBA1p-MCRsa1-FBA1t: Eno2p-HiBADH-Eno2t: TPI1p-EUTE-TPI1t |
| YBC-1693 | ald2Δ-g4423p(1kb)-MCRsa1-TEF1t: TDH3p-BDH-TDH3t: PDC1p-EutE-PDC1t |

As a result, as shown in FIG. 8, it was confirmed that the expression level of the MCRsa1 gene in the constructed recombinant strain was similar to that of the g4423 gene, and was much higher than that in the strain (control YBC-061) containing the TEFL promoter that is a strong promoter derived from S. cerevisiae.

The promoter of G4423 was compared with the promoters of various ADH isozymes derived from S. cerevisiae used in the past, and as a result of comparing homology, it was found that the homology was very low (Table 8). The comparison of homology between the promoter of G4423 and the promoters of various conventional ADH isozymes derived from S. cerevisiae was performed, and as a result, it could be seen that the homology was very low (Table 8).

TABLE 8

Comparison of homology between g4423 promoter region and S. cerevisiae ADH promoter regions

| Target gene | Adh1p | Adh2p | Adh3p | Adh4p | Adh5p | Adh6p | Adh7p | SFA1p |
|---|---|---|---|---|---|---|---|---|
| Percent identity | 28.06 | 29.71 | 24.48 | 27.63 | 31.44 | 29.02 | 28.05 | 29.47 |

Example 6: Production of 3-HP in Recombinant Strain Constructed by Replacing g4423 Gene with MCRsa1 Gene Analysis was performed as to the production amount of 3-HP in the recombinant YBC-1684 confirmed to have an increased expression level of the MCR gene in Example 5.

Comparison with the results in Table 3 of Example was performed. As shown in Table 3 above, when the three core genes related to 3-HP production were expressed using the scTEF promoter or the FBA promoter, about 1 to 16 mg/L of 3-HP was produced in flask culture.

In addition, analysis was performed as to the production amounts of 3-HP in the recombinant strain YBC-1684 and a strain constructed by inserting 3-HP production-related genes into the YBC-1684 strain in which the g4423 site was replaced with MCRsa1 which was expressed.

Each of the strains was cultured with a YP medium (20 g/L peptone, and 10 g/L yeast extract) supplemented with 4% glucose and 15 μM cerulenin in a flask at 30° C., and on day 5 when sugar was completely consumed, the culture medium was sampled and the production of 3-HP was analyzed.

As a result, as shown in Table 9 below, the YBC-1684 strain in which only the MCRsa1 gene was inserted into the g4423 site produced 200 mg/L of 3-HP, and the strain in which the 3-HP production-related genes (HiBADH gene and EUTE gene) were additionally inserted into the g4423 site produced 146 to 710 mg/L of 3-HP, which was different between colonies. Thus, it could be confirmed that production of 3-HP in this strain was significantly higher than production of 3-HP in the recombinant strain in which the corresponding gene was expressed by the scTEF promoter or the FBA promoter.

TABLE 9

|  | Control | YBC-1684 | YBC-trans (multiple colonies) |
|---|---|---|---|
| 3-HP concentration at 5 days (mg/L) | 0 | 200 | 342 46 to 710) |

From these results, it was confirmed that the increased expression of the MCRsa1 gene by the g4423 promoter could have a great influence on the increased production of 3-HP. Thereby, it could be seen that, if the expression of genes involved in a target compound is increased by the g4423 promoter, the production of the target compound can increase.

Example 7: Analysis of Mobility of g4423 Promoter

The G4423 promoter and the terminator region in the genomic DNA of the YBC strain were cut into a length of 1 kb, and the expression level of the MCRsa1 gene for 3-HP production was analyzed. Based on information on g4423 and UTR in the genome of the YBC strain, the 1 kb region of the 5'UTR region of g4423 was amplified using primers and extracted, and then amplified using the oSK-1412 to oSK1419 primers of Table 2 above, thus obtaining an MCRsa1 fragment optimized for yeast codon usage with the promoter of g4423. The obtained fragment was introduced into the cassette of FIG. 1(e) capable of expressing a plurality of genes, and the plasmid (pSK-865) used is set forth in SEQ ID NO: 8. The donor DNA cassette was amplified, purified and introduced into YBC, and the genotype of the grown colonies was analyzed.

It was confirmed that the expression level of MCRsa1 in the recombinant strain YBC-1693 conducted by the above method was lowered, like when the promoter (FBA) of YBC or the TEF1p promoter of S. cerevisiae was used (FIG. 9). Thus, it is presumed that the promoter action of the YBC acid-resistant strain requires a longer fragment or has mechanisms that act even at a long distance (enhancer or silencer) or mechanisms that work in combination by multiple factors. Additional research is needed to accurately elucidate these mechanisms.

When the g4423 gene is replaced with a target gene, two effects can be obtained: the target gene can be strongly expressed, and the g4423 gene that is involved in ethanol production is removed. Thus, it is possible to effectively accomplish the purpose of research to produce various compounds using the strain.

Example 8: Expression of LDH Gene by g4423 Promoter

In this Example, a recombinant YBC strain was constructed, in which the LDH (lactate dehydrogenase) gene involved in lactate production in addition to the MCR gene was replaced with the g4423 gene. The lactate productivity of the constructed strain was analyzed.

The recombinant strain was constructed so that three representative genes (*L. helveticus*-derived LDH, *R. oryzae*-derived LDH, and *L. plantarum*-derived LDH) would be expressed by the g4423 promoter.

Based on information on g4423 and UTR, a gene cassette similar to that shown in FIG. 1(*e*) was constructed, in which the g4423 ORF was removed and which had 5' and 3' UTRs and an antibiotic marker. Based on information on three genes from the NCBI, sequences optimized for yeast codon usage were synthesized, and then introduced into the cassette using restriction enzymes (ApaI and SacI). The donor DNA in the completed cassette was amplified and introduced into the YBC strain. The grown colonies were analyzed using the following primers for identifying the g4423 ORF, and as a result, it was confirmed that one allele of the g4423 ORF was removed and each of the LDH genes was introduced.

```
L. helveticus forward primer (SEQ ID NO: 76):
ATGAAAATTTTTGCTTATGG;

L. helveticus reverse primer (SEQ ID NO: 77):
TTAATATTCAACAGCAATAG;

R. oryzae forward primer (SEQ ID NO: 78):
ATGGTTTTGCATTCTAAAGT;

R. oryzae reverse primer (SEQ ID NO: 79):
TTAACAAGAAGATTTAGAAA;

L. plantarum forward primer (SEQ ID NO: 80):
ATGTCTTCTATGCCAAATCA;

L. plantarum reverse primer (SEQ ID NO: 81):
TTATTTATTTTCCAATTCAG
```

The constructed recombinant strain was shake-cultured with YP (20 g/L peptone, and 10 g/L yeast extract) medium supplemented with 4% glucose and 150 mg/L uracil at 30° C. and 100 rpm for 24 hours.

Lactate and ethanol in the culture medium were analyzed by HPLC. The concentrations of glucose, ethanol and L-lactate in the culture medium were analyzed using a Bio-Rad Aminex 87-H column with a Waters 1525 Binary HPLC pump. Glucose and ethanol were analyzed using a Waters 2414 refractive index detector, and L-lactate was analyzed using a Waters 2489 UV/visible detector (210 nm). The concentration of each component was calculated using a peak area standard curve plotted according to the concentration of each component, and specific conditions for analysis are as follows.

1. Mobile phase condition: 0.005M $H_2SO_4$ solution
2. Flow rate: 0.6 mL/min
3. Run time: 40 min
4. Column oven temperature: 60° C.
5. Detector temperature: 40° C.
6. Injection volume: 10 μL
7. Auto sampler tray temperature: 4° C.

As a result, as shown in FIG. 10, it was confirmed that the replaced target genes exhibited LDH activity, so that lactate was produced.

[Depository Information]
Name of Depositary Authority: Korea Research Institute of Bioscience and Biotechnology
Accession Number: KCTC13508BP
Deposit Date: Apr. 11, 2018

INDUSTRIAL APPLICABILITY

When an organic acid production-related target gene is expressed in an organic acid-resistant yeast using the novel promoter according to the present invention, there is an advantage in that the yeast can produce the organic acid with high efficiency while having resistance to organic acids without inhibiting the growth ability of the yeast.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

Sequence List Free Text
Electronic file is attached

---

The invention claimed is:

1. A recombinant microorganism having an isolated promoter comprising the nucleotide sequence of SEQ ID NO: 1 or SEQ ID NO: 2.

2. The recombinant microorganism of claim 1, further containing an isolated terminator comprising the sequence of SEQ ID NO: 3 or SEQ ID NO: 4.

3. The recombinant microorganism of claim 1, which is yeast.

4. The recombinant microorganism of claim 3, wherein the yeast is YBC, deposited under Accession No. KCTC13508BP.

5. A method for producing an organic acid, the method comprising steps of:

(a) producing the organic acid by culturing the recombinant microorganism of claim 1 introduced therein; and (b) collecting the produced organic acid.

6. A recombinant microorganism having a gene construct in which an isolated promoter comprising the nucleotide sequence comprising SEQ ID NO: 1 or SEQ ID NO: 2 and a gene encoding a target gene are operably linked to each other in an acid-resistant yeast YBC strain deposited under Accession No. KCTC13508BP.

7. The recombinant microorganism of claim 6, further containing an isolated terminator comprising the sequence of SEQ ID NO: 3 or SEQ ID NO: 4.

8. The recombinant microorganism of claim 6, further containing a malonyl-CoA-reductase coding gene or lactate dehydrogenase coding gene involved in organic acid production.

9. A method for producing an organic acid, the method comprising steps of:
(a) producing the organic acid by culturing the recombinant microorganism of claim 6 introduced therein; and
(b) collecting the produced organic acid.

* * * * *